US009820845B2

(12) United States Patent
von Lehe et al.

(10) Patent No.: US 9,820,845 B2
(45) Date of Patent: Nov. 21, 2017

(54) HOLDING ZONE FOR INTRAVASCULAR MEDICAL DEVICE

(71) Applicant: Covidien LP, Mansfield, MA (US)

(72) Inventors: Cathleen von Lehe, Rogers, MN (US); Richard S. Kusleika, Excelsior, MN (US); Brooke Ren, Maple Grove, MN (US); Thomas L. Clubb, Hudson, WI (US)

(73) Assignee: Covidien LP, Mansfield, MA (US)

( * ) Notice: Subject to any disclaimer, the term of this patent is extended or adjusted under 35 U.S.C. 154(b) by 8 days.

(21) Appl. No.: 14/981,490

(22) Filed: Dec. 28, 2015

(65) Prior Publication Data

US 2016/0128821 A1    May 12, 2016

Related U.S. Application Data

(63) Continuation of application No. 13/746,429, filed on Jan. 22, 2013, now Pat. No. 9,220,873, which is a continuation of application No. 12/620,212, filed on Nov. 17, 2009, now Pat. No. 8,435,256, which is a continuation of application No. 10/810,445, filed on Mar. 26, 2004, now Pat. No. 7,637,920.

(60) Provisional application No. 60/508,437, filed on Oct. 3, 2003, provisional application No. 60/458,884, filed on Mar. 28, 2003.

(51) Int. Cl.
| | | |
|---|---|---|
| *A61M 29/00* | (2006.01) | |
| *A61F 2/01* | (2006.01) | |
| *A61M 25/09* | (2006.01) | |
| *A61M 25/00* | (2006.01) | |

(52) U.S. Cl.
CPC ............... *A61F 2/01* (2013.01); *A61F 2/013* (2013.01); *A61M 25/0023* (2013.01); *A61M 25/09* (2013.01); *A61F 2002/011* (2013.01); *A61F 2002/018* (2013.01); *A61F 2230/008* (2013.01); *A61F 2230/0008* (2013.01); *A61M 25/00* (2013.01)

(58) Field of Classification Search
CPC .......... A61F 2/01; A61F 2/013; A61M 25/00; A61M 25/09; A61M 25/0023; A61M 29/00; A61B 17/22
See application file for complete search history.

(56) References Cited

U.S. PATENT DOCUMENTS

| | | |
|---|---|---|
| 4,762,129 A | 8/1988 | Bonzel |
| 4,991,602 A | 2/1991 | Amplatz et al. |
| 5,059,183 A | 10/1991 | Semrad |
| 5,069,225 A | 12/1991 | Okamura |
| 5,112,327 A | 5/1992 | Iinuma et al. |

(Continued)

FOREIGN PATENT DOCUMENTS

| | | |
|---|---|---|
| EP | 0516189 | 10/1989 |
| EP | 0364777 | 4/1990 |

(Continued)

OTHER PUBLICATIONS

Prosecution History from U.S. Appl. No. 13/746,429, dated Dec. 4, 2014 through Dec. 9, 2015, 45 pp.

(Continued)

*Primary Examiner* — Victor Nguyen

(57) ABSTRACT

A catheter that includes storage for an embolic protection device in an accessible, out-of-the-way location within the advancing catheter.

20 Claims, 27 Drawing Sheets

(56) References Cited

U.S. PATENT DOCUMENTS

| | | | |
|---|---|---|---|
| 5,176,626 A | 1/1993 | Soehendra | |
| 5,217,025 A | 6/1993 | Okamura | |
| 5,363,847 A | 11/1994 | Viera | |
| 5,498,240 A | 3/1996 | Bagaoisan et al. | |
| 5,531,700 A | 7/1996 | Moore | |
| 5,662,703 A * | 9/1997 | Yurek | A61F 2/95 606/194 |
| RE35,849 E | 7/1998 | Soehendra | |
| 5,910,154 A | 6/1999 | Tsugita | |
| 5,911,734 A | 6/1999 | Tsugita | |
| 5,925,059 A | 7/1999 | Palermo et al. | |
| 6,027,520 A | 2/2000 | Tsugita | |
| 6,042,598 A | 3/2000 | Tsugita | |
| 6,045,547 A | 4/2000 | Ren et al. | |
| 6,096,022 A | 8/2000 | Laymon et al. | |
| 6,152,946 A | 11/2000 | Broome et al. | |
| 6,165,200 A | 12/2000 | Tsugita | |
| 6,171,327 B1 | 1/2001 | Daniel | |
| 6,245,089 B1 | 6/2001 | Daniel | |
| 6,270,513 B1 | 8/2001 | Tsugita | |
| 6,325,815 B1 | 12/2001 | Kusleika et al. | |
| 6,361,546 B1 | 3/2002 | Khosravi | |
| 6,371,969 B1 | 4/2002 | Tsugita | |
| 6,371,971 B1 | 4/2002 | Tsugita | |
| 6,485,501 B1 | 11/2002 | Green | |
| 6,520,978 B1 | 2/2003 | Blackledge | |
| 6,537,295 B2 | 3/2003 | Petersen | |
| 6,537,297 B2 | 3/2003 | Tsugita | |
| 6,544,279 B1 | 4/2003 | Hopkins | |
| 6,544,280 B1 | 4/2003 | Daniel et al. | |
| 6,595,960 B2 | 7/2003 | West et al. | |
| 6,616,680 B1 | 9/2003 | Thielen | |
| 6,652,505 B1 | 11/2003 | Tsugita | |
| 6,663,651 B2 | 12/2003 | Kralik | |
| 6,663,652 B2 | 12/2003 | Daniel | |
| 6,676,682 B1 | 1/2004 | Tsugita | |
| 6,679,902 B1 | 1/2004 | Boyle | |
| 6,689,151 B2 | 2/2004 | Becker | |
| 6,752,819 B1 | 6/2004 | Brady | |
| 6,793,666 B2 | 9/2004 | Hansen | |
| 6,837,898 B2 | 1/2005 | Boyle | |
| 6,872,216 B2 | 3/2005 | Daniel | |
| 6,887,256 B2 | 5/2005 | Gilson | |
| 6,887,257 B2 | 5/2005 | Salahieh | |
| 6,929,652 B1 | 8/2005 | Andrews | |
| 6,936,059 B2 | 8/2005 | Belef | |
| 6,964,673 B2 | 11/2005 | Tsugita | |
| 6,974,469 B2 | 12/2005 | Broome | |
| 6,979,343 B2 | 12/2005 | Russo et al. | |
| 6,991,642 B2 | 1/2006 | Petersen | |
| 6,997,938 B2 | 2/2006 | Wang | |
| 7,056,328 B2 | 6/2006 | Arnott | |
| 7,637,920 B2 | 12/2009 | Von Lehe et al. | |
| 8,435,256 B2 | 5/2013 | von Lehe et al. | |
| 9,220,873 B2 | 12/2015 | von Lehe et al. | |
| 2001/0041909 A1 | 11/2001 | Tsugita | |
| 2002/0042626 A1 | 4/2002 | Hanson | |
| 2002/0049467 A1 | 4/2002 | Gilson | |
| 2002/0082639 A1 | 6/2002 | Broome | |
| 2002/0095141 A1 | 7/2002 | Belef | |
| 2002/0111649 A1 | 8/2002 | Russo | |
| 2002/0121472 A1 | 9/2002 | Garner | |
| 2002/0128678 A1 | 9/2002 | Petersen | |
| 2002/0128681 A1 | 9/2002 | Broome | |
| 2003/0065356 A1 | 4/2003 | Tsugita | |
| 2003/0083693 A1 | 5/2003 | Daniel | |
| 2003/0130685 A1 | 7/2003 | Daniel | |
| 2003/0130686 A1 | 7/2003 | Daniel | |
| 2003/0130687 A1 | 7/2003 | Daniel | |
| 2003/0176887 A1 | 9/2003 | Petersen | |
| 2003/0181943 A1 | 9/2003 | Daniel | |
| 2003/0187474 A1 | 10/2003 | Keegan | |
| 2003/0187475 A1 | 10/2003 | Tsugita | |
| 2003/0233117 A1 | 12/2003 | Adams et al. | |
| 2004/0019363 A1 | 1/2004 | Hanson | |
| 2004/0049226 A1 | 3/2004 | Keegan | |
| 2004/0106944 A1 | 6/2004 | Daniel | |
| 2004/0127934 A1 | 7/2004 | Gilson | |
| 2004/0167566 A1 | 8/2004 | Beulke | |
| 2005/0090810 A1 | 4/2005 | Petersen | |
| 2005/0101986 A1 | 5/2005 | Daniel | |
| 2005/0113804 A1 | 5/2005 | von Lehe et al. | |
| 2005/0113865 A1 | 5/2005 | Daniel | |
| 2005/0119691 A1 | 6/2005 | Daniel | |
| 2005/0131449 A1 | 6/2005 | Salahieh | |
| 2005/0228437 A1 | 10/2005 | Gilson | |
| 2005/0228439 A1 | 10/2005 | Andrews | |
| 2005/0234502 A1 | 10/2005 | Gilson | |
| 2006/0004403 A1 | 1/2006 | Gilson | |
| 2006/0015140 A1 | 1/2006 | Tsugita | |
| 2006/0047266 A1 | 3/2006 | Elkins | |
| 2006/0095005 A1 | 5/2006 | Quinn | |
| 2006/0100662 A1 | 5/2006 | Daniel | |
| 2006/0129181 A1 | 6/2006 | Callol et al. | |

FOREIGN PATENT DOCUMENTS

| | | |
|---|---|---|
| EP | 0365269 | 4/1990 |
| EP | 0516198 | 12/1992 |
| EP | 0516198 A1 | 12/1992 |
| EP | 0761250 | 3/1997 |
| EP | 1351737 | 10/2003 |
| EP | 1598089 A1 | 11/2005 |
| WO | WO96/01591 | 1/1996 |
| WO | 9839053 | 9/1998 |
| WO | 9850103 | 11/1998 |
| WO | 9944542 | 9/1999 |
| WO | 9951167 | 10/1999 |
| WO | WO01/70097 | 9/2001 |
| WO | 0180776 A1 | 11/2001 |
| WO | 0180777 A2 | 11/2001 |
| WO | 02069844 A2 | 9/2002 |
| WO | 02069845 A2 | 9/2002 |
| WO | 2005058196 A2 | 6/2005 |

OTHER PUBLICATIONS

Prosecution History from U.S. Appl. No. 12/620,212, dated Mar. 3, 2011 through Jan. 7, 2013, 44 pp.

Prosecution History from U.S. Appl. No. 10/810,445, dated Aug. 13, 2004 through Apr. 21, 2010, 71 pp.

Prosecution History from U.S. Appl. No. 10/917,249, dated Jan. 24, 2008 through Dec. 2, 2008, 8 pp.

Chester, "Permanent Transrectal Drainage of a Diverticular-Related Abscess With a Double-Ended Pigtail Catheter," Br J Surg. 75(6): 562 (Jun. 1988).

Cox, "Percutaneous Cystogastrostomy for Treatment of Pancreatic Pseudocysts," Aust N 2 J Surg, 63(9): 693-698 (Sep. 1993).

Feb. 28, 2005 Notification of Transmittal of the International Search Report and the Written Opinion of the International Searching Authority, or the Declaration in PCT/US2004/009518 (15 pages).

Sep. 28, 2004 Invitation to Pay Additional Fees and Partial International Search Report in PCT/US2004/009518 (5 pages).

\* cited by examiner

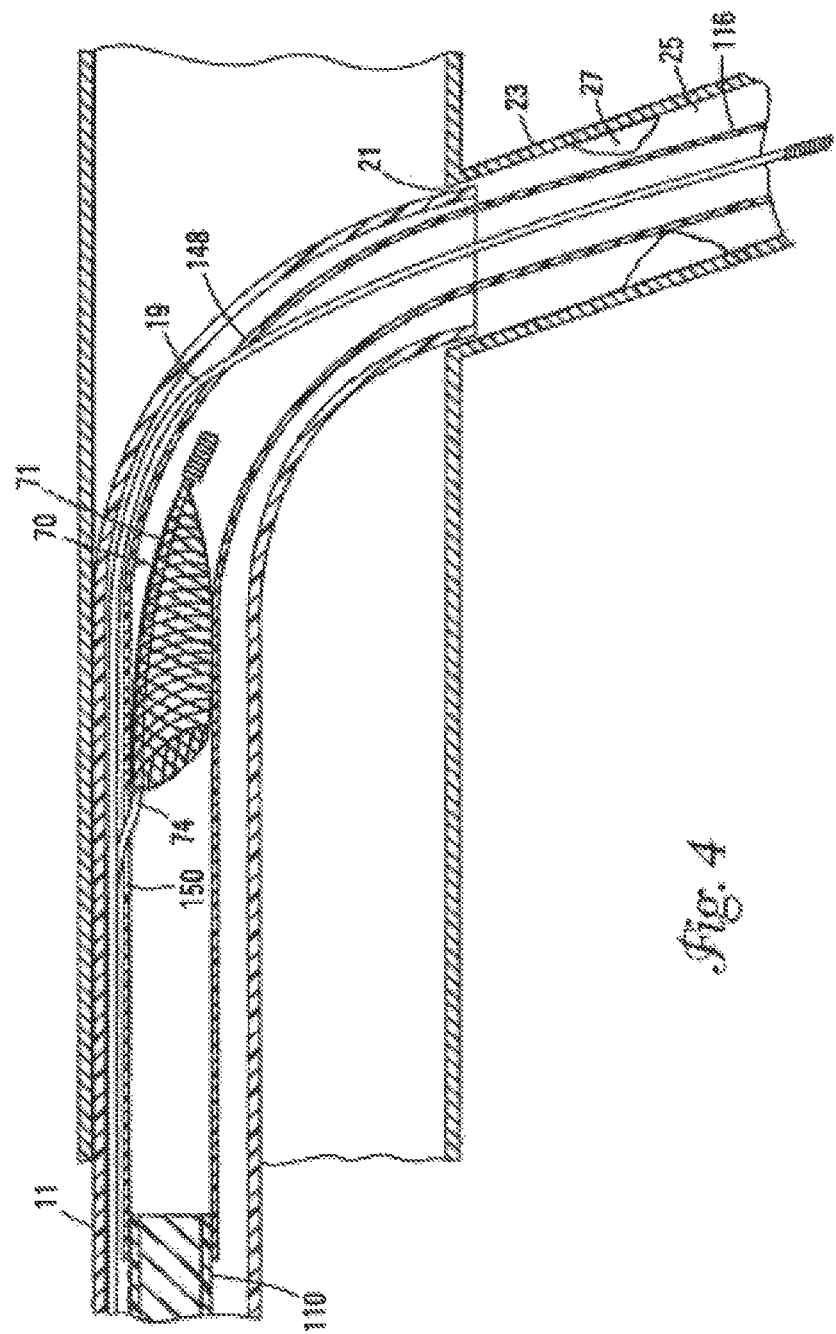

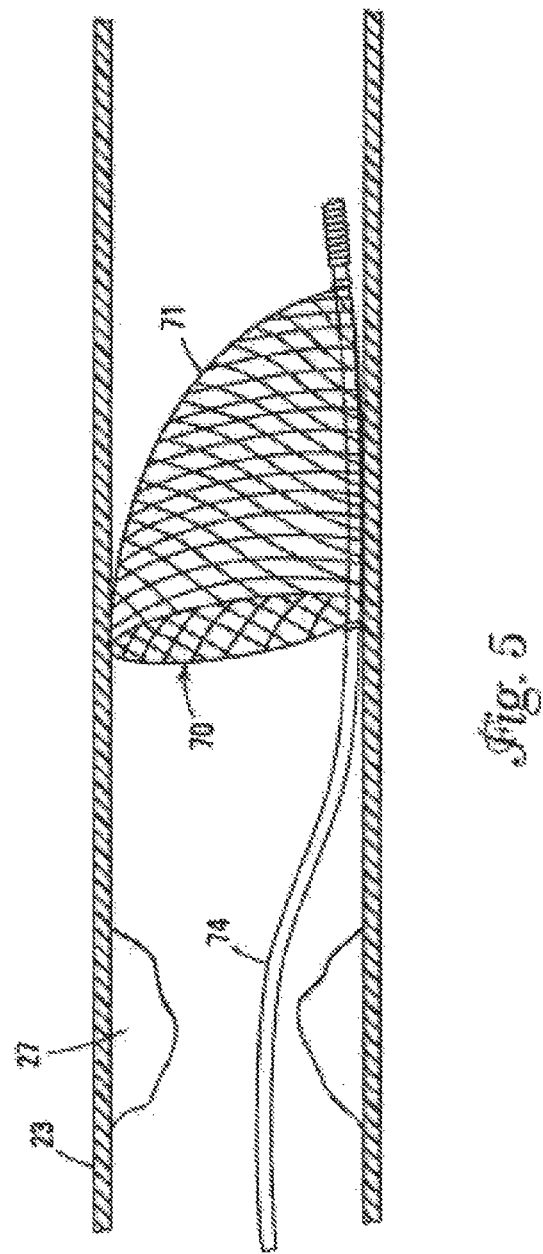

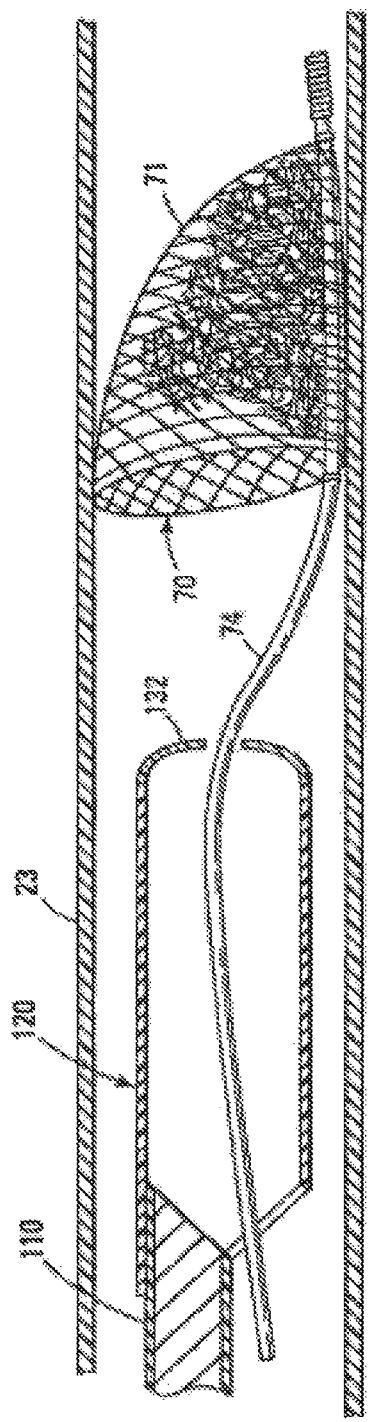

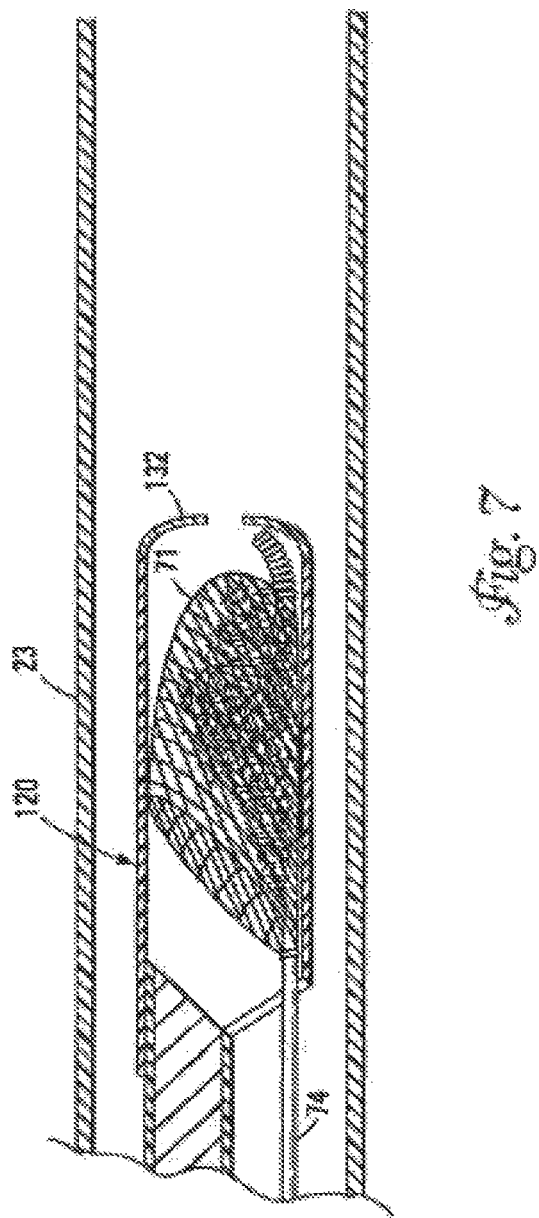

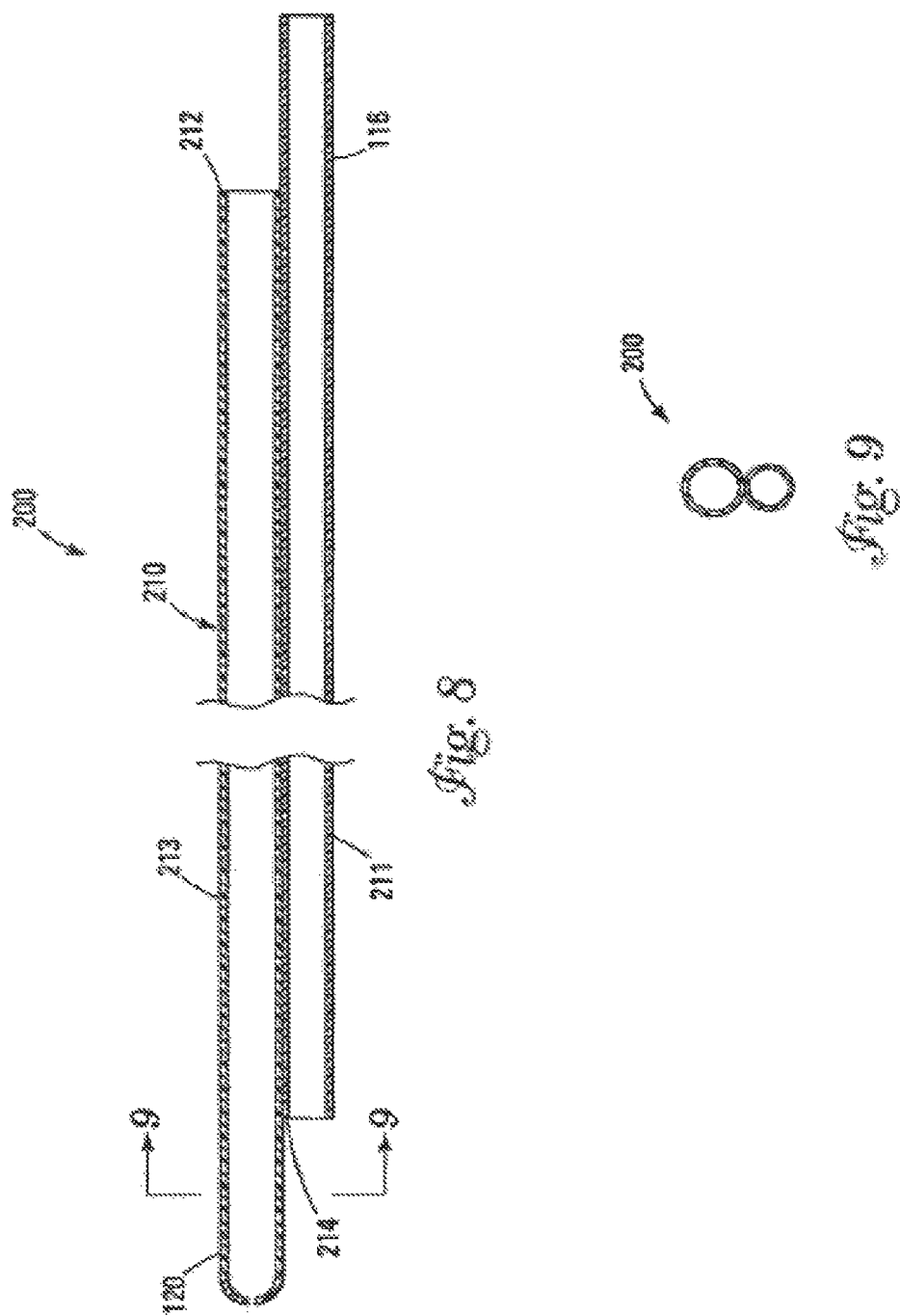

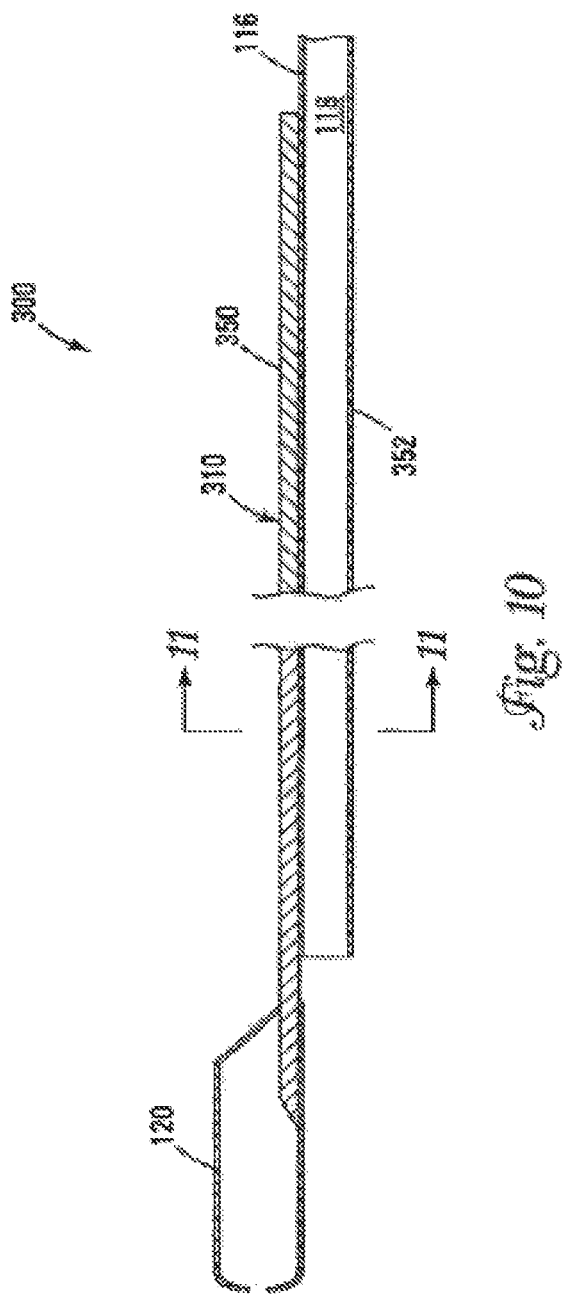
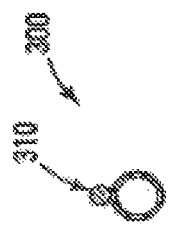

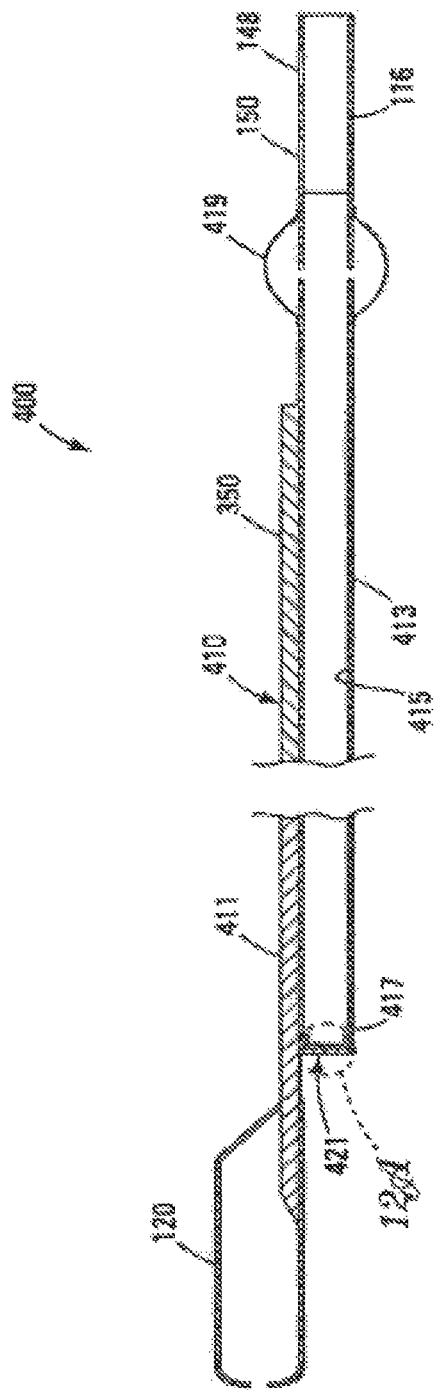
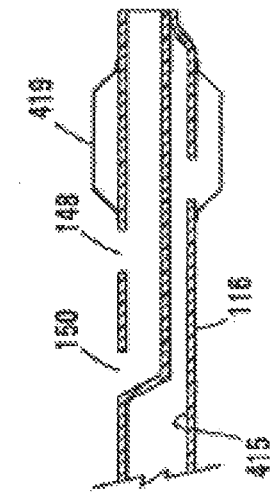
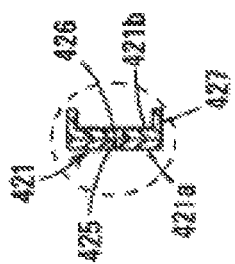
Fig. 12
Fig. 12B
Fig. 12A

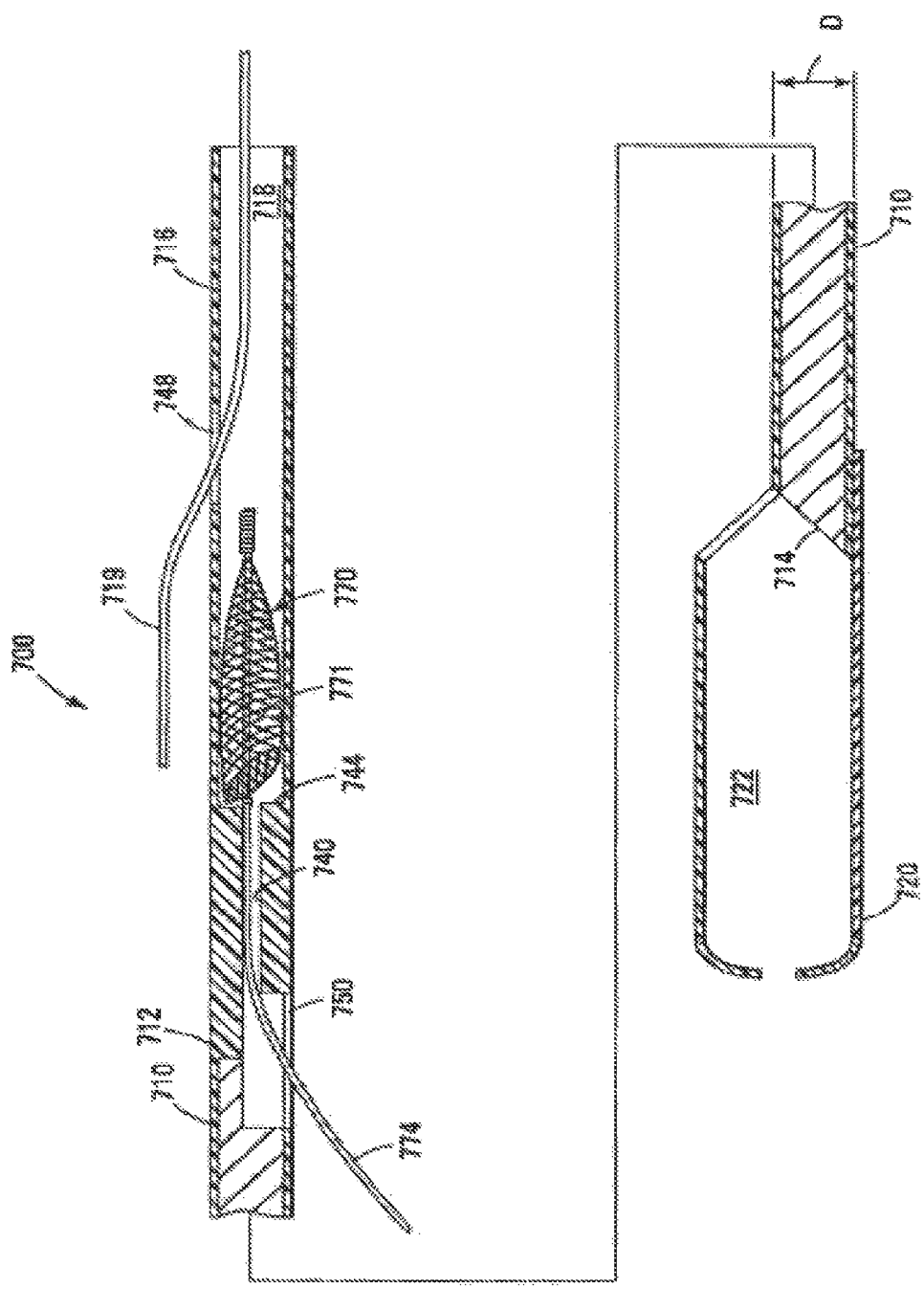

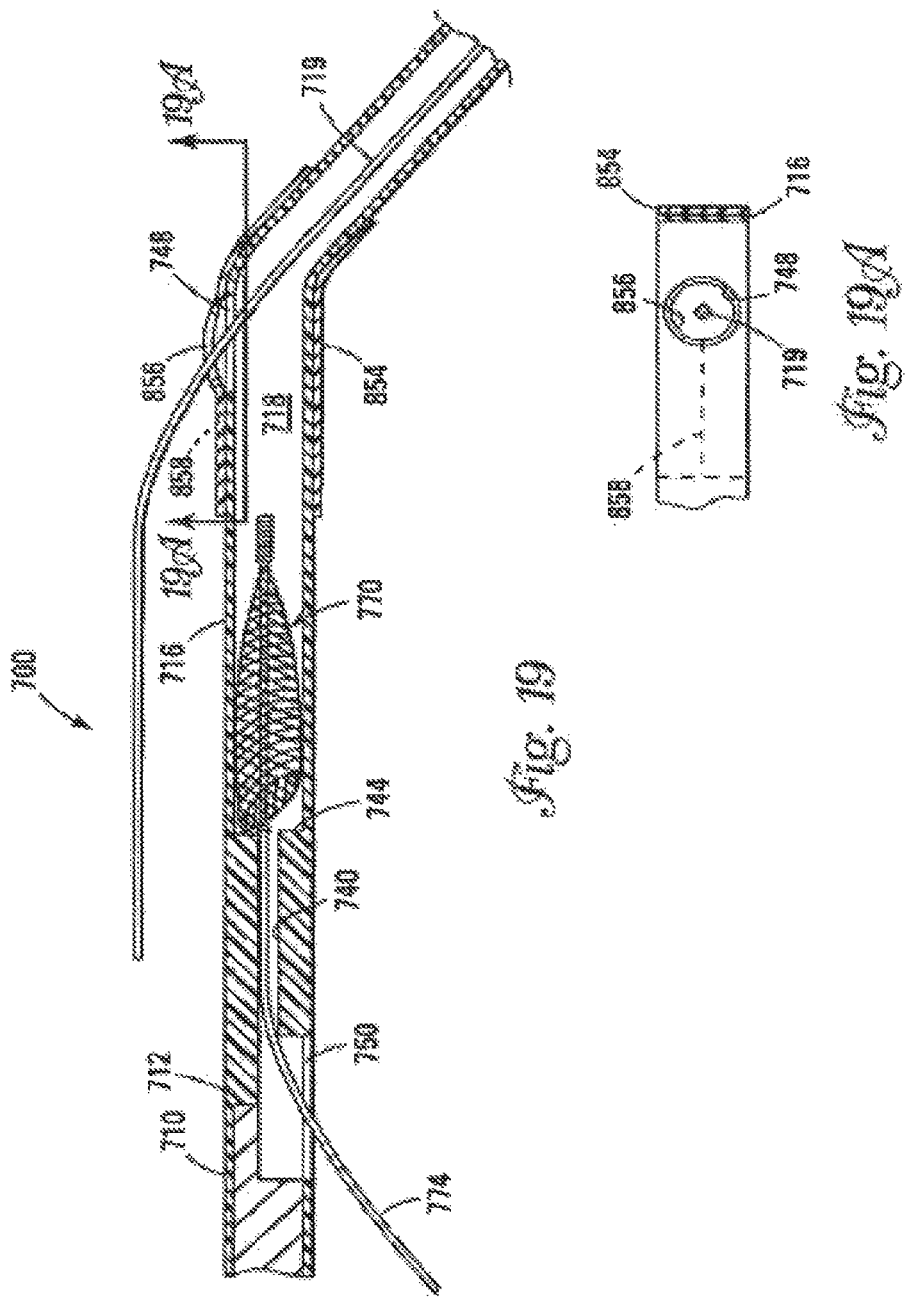

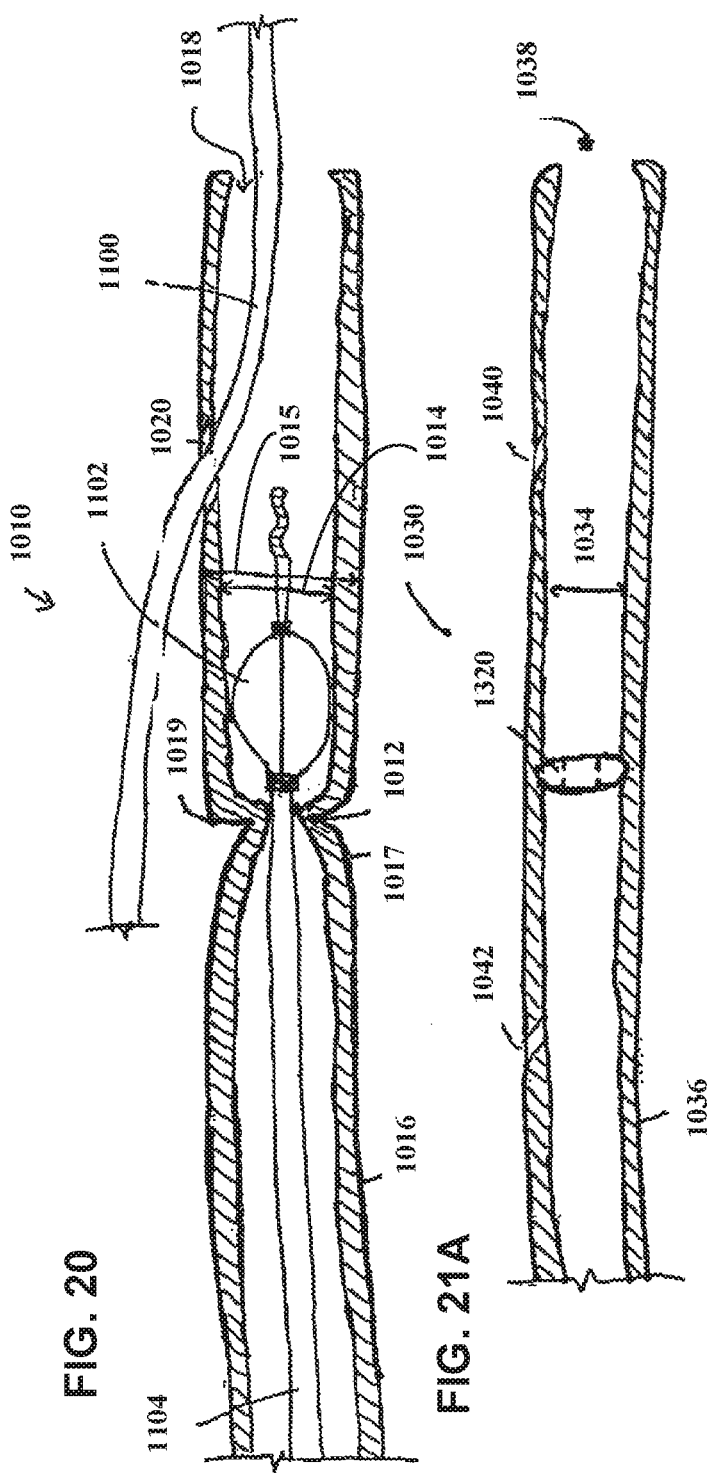

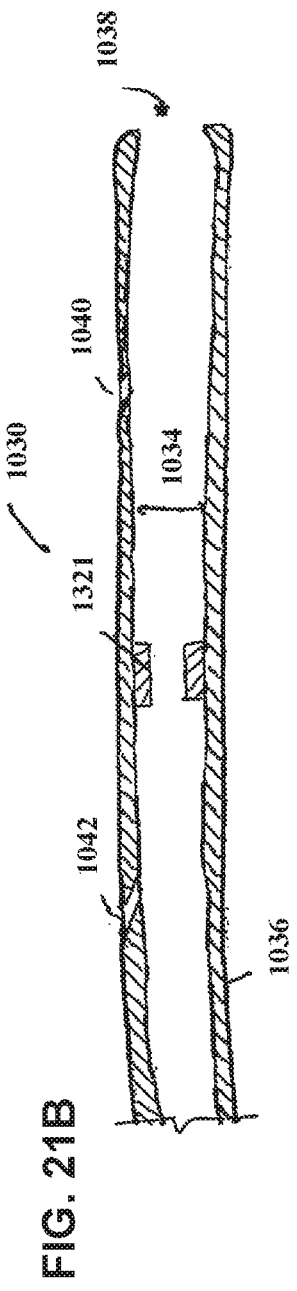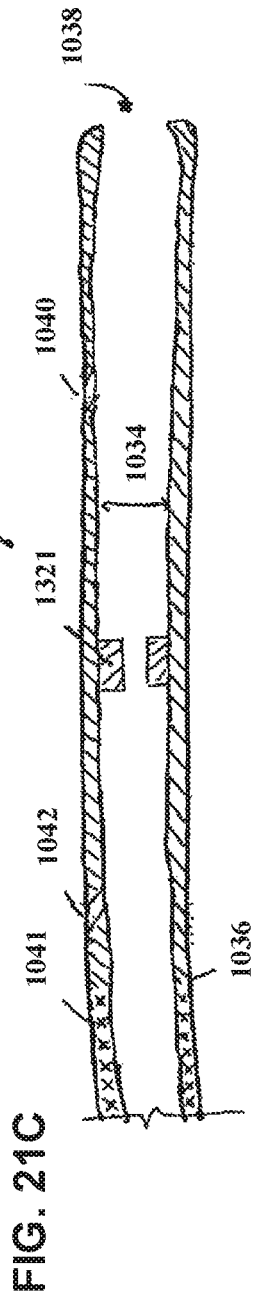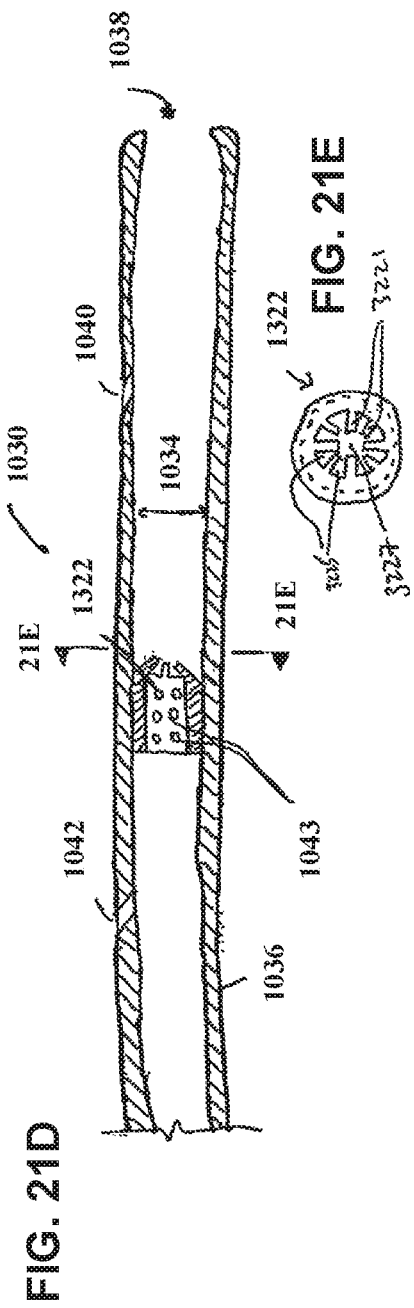

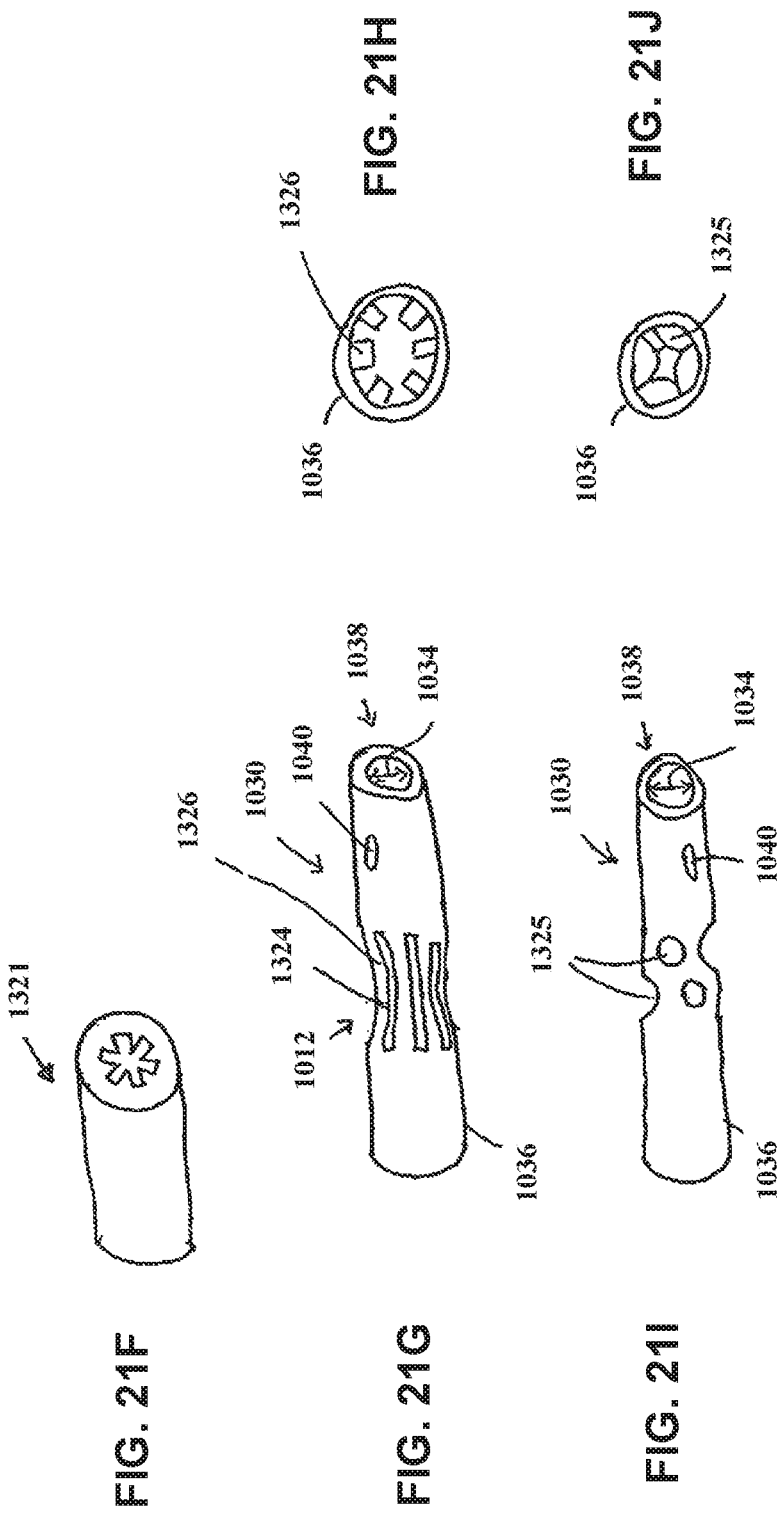

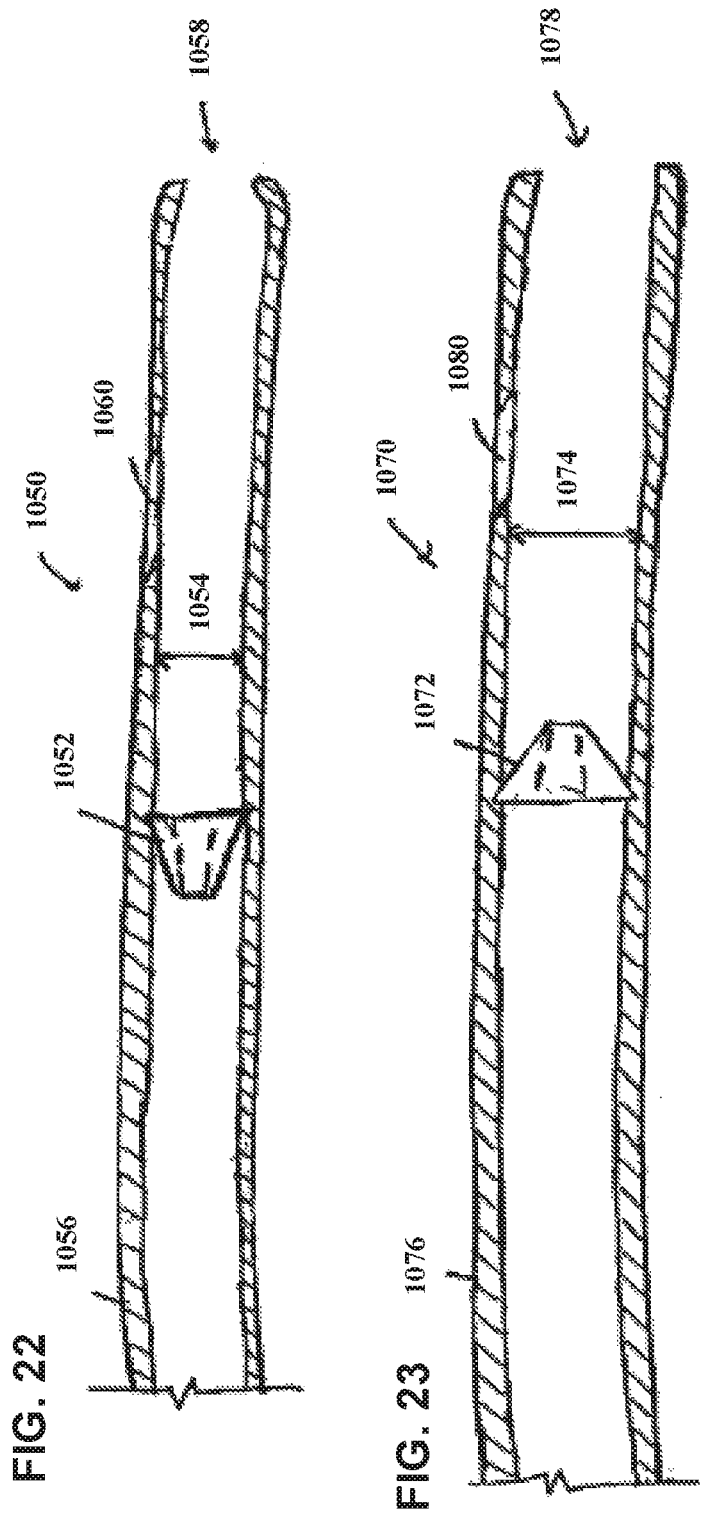

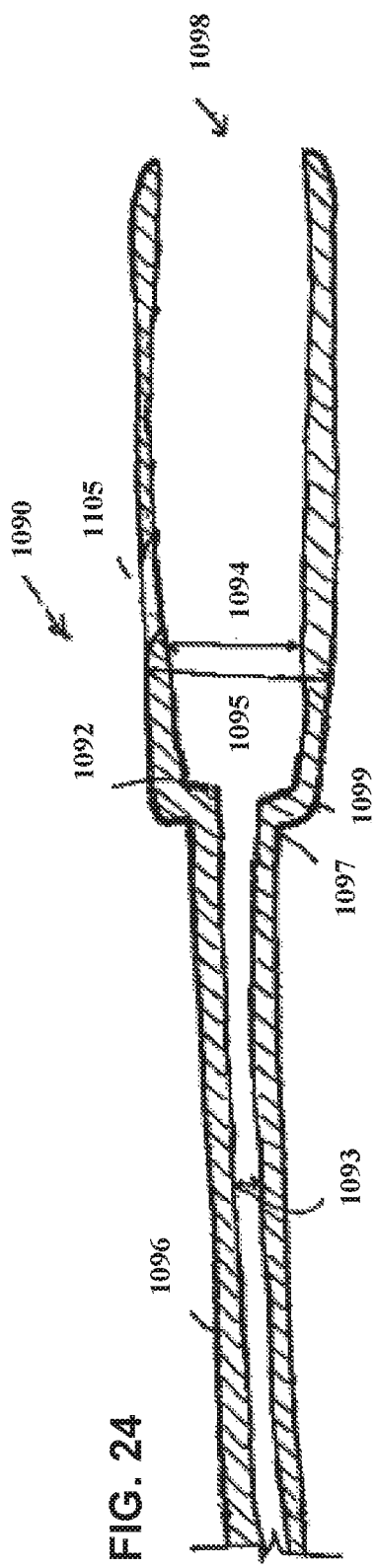
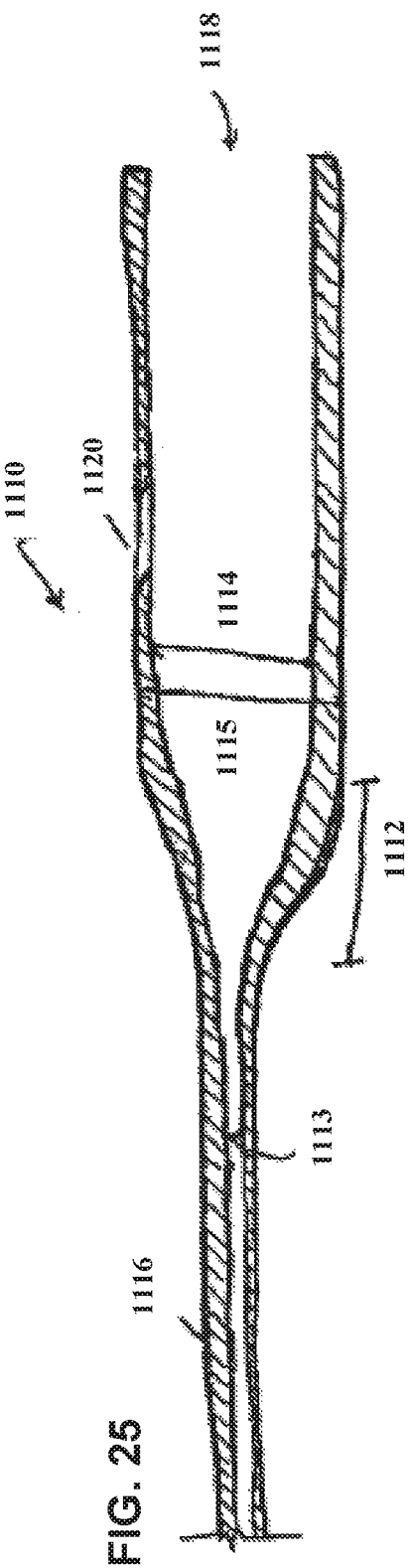

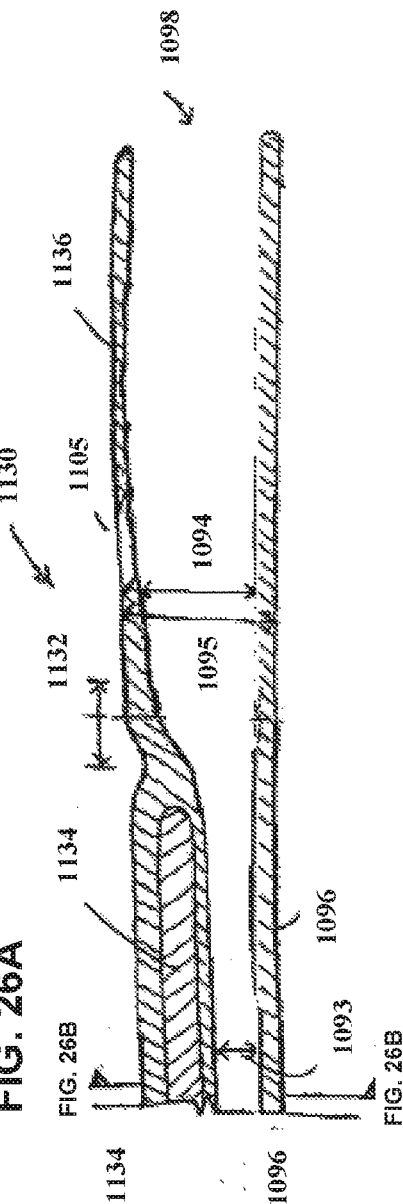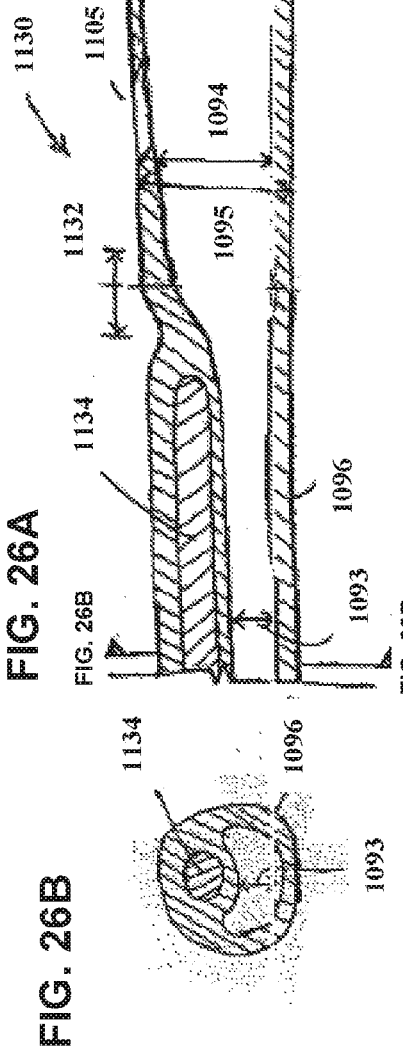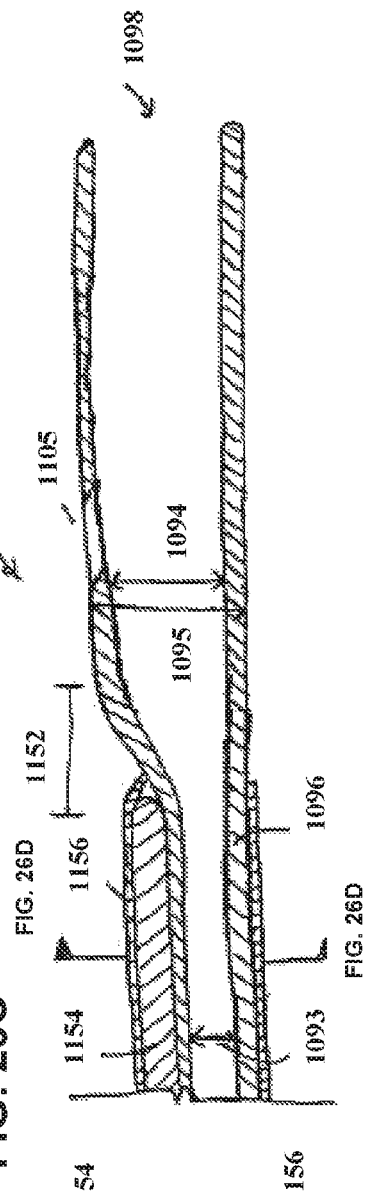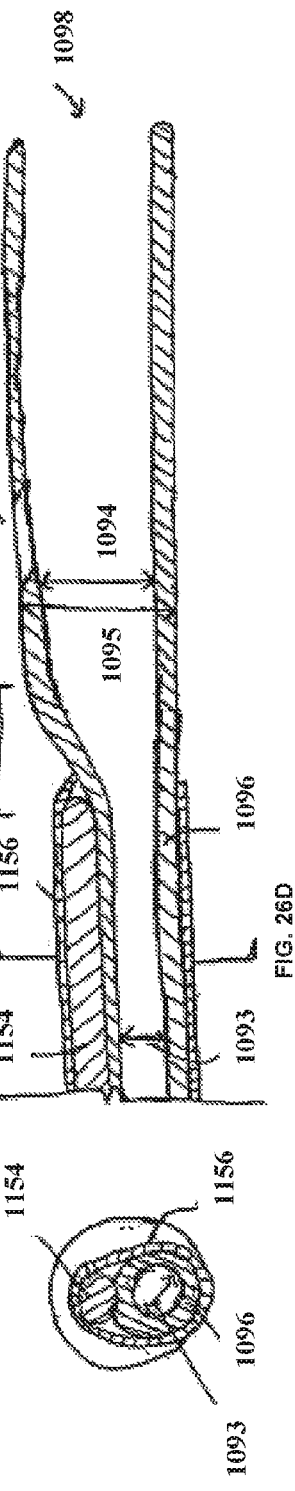

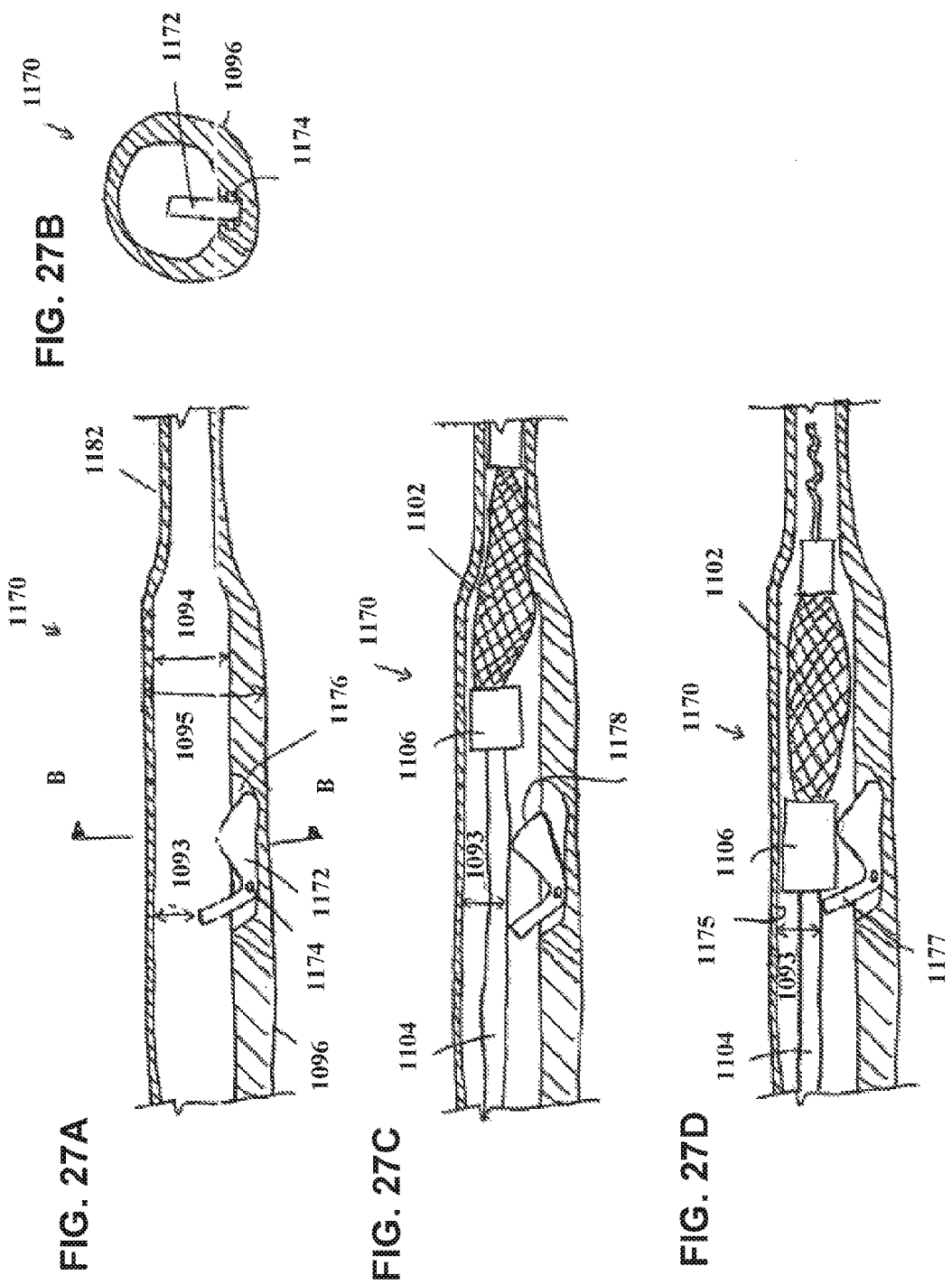

HOLDING ZONE FOR INTRAVASCULAR MEDICAL DEVICE

CROSS-REFERENCE TO RELATED APPLICATIONS

This application is a continuation of U.S. patent application Ser. No. 13/746,429, filed on Jan. 22, 2013, which is a continuation of U.S. patent application Ser. No. 12/620,212, filed on Nov. 17, 2009, now U.S. Pat. No. 8,435,256, which is a continuation of U.S. patent application Ser. No. 10/810,445, filed on Mar. 26, 2004, now U.S. Pat. No. 7,637,920, which claims the benefit of, and priority to, U.S. Provisional Pat. Application Ser. Nos. 60/508,437 and 60/458,884, filed on Oct. 3, 2003 and Mar. 28, 2003, respectively, the entire content of each of the applications identified above being incorporated by reference herein.

FIELD OF THE INVENTION

The present invention is related generally to medical devices. More specifically, the present invention is related to intravascular medical devices such as catheters and guidewires.

BACKGROUND OF THE INVENTION

Blood vessel disease is a significant cause of premature disability and death. Heart attacks, strokes and other ailments are often caused by blood vessel disease.

The most common disease of the blood vessels is atherosclerosis. Atherosclerosis involves the accumulation of plaques of cholesterol, lipids and cellular debris within an artery. As the plaque accumulates, the artery wall thickens thereby narrowing the lumen of the artery. As the lumen narrows, the blood flow to tissue nourished by the artery is diminished. The development of plaques can also contribute to the formation of emboli or thrombi. An embolus is a moving obstruction such as a platelet aggregate. A thrombus can be a fixed obstruction such as a wall adherent blood clot or can become an embolus. A thrombus or embolus within a coronary artery can occlude the artery thereby causing myocardial infarction, angina and other conditions. A blockage caused by a thrombus or embolus within a vessel supplying blood to the brain can lead to a stroke. Renal, peripheral, and other blood vessels can also become blocked by an embolus or a thrombus thereby causing tissue damage downstream of the blockage.

A number of medical procedures have been developed to allow for the removal of plaque from vessel walls or to clear a channel through plaque, thrombus or clot to restore blood flow. For example, atherectomy or thrombectomy devices can be used to remove atheroma or thrombus. Vessel restrictions can also be treated with grafts that bypass the restrictions. Alternatively, balloon angioplasty and stenting procedures can be used to enlarge the lumen size of a vessel at an obstruction.

In a typical angioplasty procedure, a guide wire and guide catheter are inserted into a vessel of a patient. An inflatable balloon is then pushed through the guide catheter and advanced across a stenosis or blockage. Once positioned at the blockage, the balloon is inflated to dilate the blockage and open a flow channel through the partially blocked vessel region. One or more stents may also be placed across the dilated region or regions to reinforce the expanded vessel segment or to maintain dilatation of a vessel segment.

While some stenoses remain adherent to the vessel wall during treatment, others are more brittle, and may partially crack and fragment during treatment, allowing the fragments to flow downstream where they may block more distal and smaller vessels. Consequences of embolization include myocardial infarction, stroke, diminished renal function, and impairment of peripheral circulation possibly leading to pain and amputation.

Embolic protection devices have been developed to prevent the downstream travel of materials such as thrombi, grumous, emboli, and plaque fragments. Devices include occlusive devices and filters and may be deployed distal to a treatment site or proximal to a treatment site. Occlusive devices, for example distal inflatable balloon devices, can totally block fluid flow through the vessel. The material trapped by the inflatable devices can remain in place until removed using a method such as aspiration. Occlusive devices can also be deployed proximal to a treatment site and flow reversed or stopped at the treatment site. Following treatment emboli are carried by flow out of the vessel typically through a catheter and out of a patient. Filters can allow perfusing blood flow during the emboli capture process. The filters can be advanced downstream of a site to be treated and expanded to increase the filter area. Emboli, such as grumous or atheroma fragments, can be captured in the filter until the procedure is complete or the filter is occluded. When the capacity of the filter is reached, the filter may then be retracted and replaced.

Embolic protection devices can be delivered over guide wires and within guide catheters. The embolic protection methods are normally practiced ancillary to another medical procedure, for example angioplasty with stenting or atherectomy. The embolic protection procedure typically protects downstream regions from emboli resulting from practicing the therapeutic interventional procedure.

SUMMARY OF THE INVENTION

One inventive aspect of the present disclosure relates to a medical device comprising an elongated member configured to be advanced along a vascular path of a patient, the elongated member having opposite first and second ends, the first end and second ends both being adapted for intravascular insertion, and the first end having a different structure than the second end. The elongated member has sufficient flexibility to be advanced through a human vasculature. Preferably, the first and second ends are adapted to have different operating characteristics.

Depending on the operating characteristics needed for a particular procedure, a physician can insert either the first end portion or the second end portion of the elongated member into the patient's vasculature. The intravascular medical device can include any number of different types of devices used in the treatment of vascular disease. Example devices include guide wires, catheters, embolic protection device delivery systems and embolic protection device retrieval systems.

The invention provides a method for positioning a catheter within a patient's blood vessel, the method comprising: providing a catheter comprising an elongated member configured to be advanced along a vascular path of a patient, the elongated member having opposite first and second ends, the first end and second ends both being adapted for intravascular insertion, the first end comprising a delivery sheath, the second end comprising a retrieval sheath, the delivery sheath comprising at least one sidewall port adapted for receiving a wire, and the catheter having a lumen between the first end and the at least one sidewall port; providing a guide wire having a proximal end and a distal end; advancing the guide wire to a target site within the patient's blood vessel; and advancing the catheter over the guide wire by inserting the guide wire through the catheter lumen between the first end and the at least one sidewall port.

The invention provides a guide wire loading assist device comprising: a member having a proximal first and a distal second end and a lumen there between, the lumen being adapted to encase a catheter having a sidewall port adapted for receiving a wire; and a sidewall port in the member adapted for receiving a wire, wherein the lumen of the member has a first axial orientation from the proximal first end to the sidewall port of the member and a second axial orientation from the sidewall port of the member to the distal second end, the different axial orientations forming a bend in the lumen near the sidewall port, the sidewall port of the member being adapted to be coincident with the sidewall port of the catheter.

The invention also provides a catheter that provides storage for an embolic protection device in an accessible, out-of-the-way location within the advancing catheter. In one embodiment, the catheter comprises an elongate tubular body having a proximal portion, a distal portion, a proximal end, a distal end, a lumen extending between the proximal end and the distal end, and a tube wall disposed about the lumen. A first port is disposed in the distal portion of the tubular body and dimensioned to receive a guide wire therethrough, and the first port is formed through the tube wall. The lumen of the tubular body has a first inner diameter at the first port and a second, reduced inner diameter at a point proximal of the first port.

The invention also provides a method for positioning a catheter within a patient's blood vessel, the method comprising: providing a catheter described herein; providing a guide wire having a proximal end and a distal end; advancing the guide wire to a target site within the patient's blood vessel; and advancing the catheter over the guide wire by inserting the guide wire through the catheter lumen between the distal end and the first port.

It is to be understood that both the foregoing general description and the following detailed description are exemplary and explanatory and are intended to provide further explanation of the invention as claimed.

BRIEF DESCRIPTION OF THE DRAWINGS

FIG. 4 shows the delivery end of the catheter of FIG. 2 at a target site.

FIG. 5 shows the emboli protection device of FIGS. 3 and 4 deployed at the target site.

FIG. 6 shows the catheter of FIG. 2 with a retrieval end of the catheter in close proximity to the deployed emboli protection device of FIG. 5.

FIG. 7 shows the emboli protection device of FIG. 6 captured within the retrieval end of the catheter of FIG. 2.

FIG. 8 shows an alternative double-ended catheter.

FIG. 9 is a cross-sectional view taken along section line 9-9 of FIG. 8.

FIG. 10 shows another alternative double-ended catheter.

FIG. 11 is a cross-sectional view taken along section line 11-11 of FIG. 10.

FIG. 12 shows a double-ended catheter that includes an expandable balloon.

FIG. 12A is a detailed view of a portion of FIG. 12.

FIG. 12B is an alternative balloon catheter configuration.

FIG. 18 shows an alternative double-ended catheter.

FIGS. 19 and 19A show a guide wire loading assist device disposed on an alternative double-ended catheter.

FIG. 20 shows an embolic protection device delivery/recovery catheter with a constriction in the inner diameter of the catheter proximal of a guide wire exit port and proximal of a distal exit port.

FIG. 21A shows an embolic protection device delivery/recovery catheter with a toroid insert sized to fit the inner diameter of the catheter at the location indicated in FIG. 20.

FIG. 21B shows an embolic protection device delivery/recovery catheter with a tubular insert sized to fit the inner diameter of the catheter.

FIG. 21C shows an embolic protection device delivery/recovery catheter with a tubular insert sized to fit the inner diameter of the catheter and a reinforced catheter shaft.

FIG. 21D shows an embolic protection device delivery/recovery catheter with an alternate tubular insert sized to fit the inner diameter of the catheter.

FIG. 21E shows an end view of the tubular insert shown in FIG. 21D.

FIG. 21F shows an alternate tubular insert sized to fit the inner diameter of the catheter.

FIG. 21G shows an embolic protection device delivery/recovery catheter with an alternate constriction in the inner diameter of the catheter proximal of a guide wire exit port and proximal of a distal exit port.

FIG. 21H shows an end view of the alternate constriction in the inner diameter of the catheter shown in FIG. 21G.

FIG. 21I shows an embolic protection device delivery/recovery catheter with an alternate constriction in the inner diameter of the catheter proximal of a guide wire exit port and proximal of a distal exit port.

FIG. 21J shows an end view of the alternate constriction in the inner diameter of the catheter shown in FIG. 21.

FIG. 22 shows an embolic protection device delivery/recovery catheter with a funnel-shaped insert having its larger outer diameter sized to fit the inner diameter of the catheter at the location indicated in FIG. 20, with the smaller funnel diameter facing proximally.

FIG. 23 shows an embolic protection device delivery/recovery catheter with a funnel-shaped insert as illustrated in FIG. 22, with the smaller funnel diameter facing distally.

FIG. 24 shows an embolic protection device delivery/recovery catheter with an abrupt change in inner diameter.

FIG. 25 shows an embolic protection device delivery/recovery catheter with a gradual change in inner diameter.

FIG. 26A shows an embolic protection device delivery/recovery catheter with a change in inner diameter and a proximal shaft stiffener.

FIG. 26B shows a section view of the catheter shown in FIG. 26A.

FIG. 26C shows an alternate construction of an embolic protection device delivery/recovery catheter with a change in inner diameter and a proximal shaft stiffener.

FIG. 26D shows a section view of the catheter shown in FIG. 26C.

FIG. 27A shows an embolic protection device delivery/recovery catheter with a toggle stop and a distal reduced diameter region.

FIG. 27B shows a section view of the catheter shown in FIG. 27A.

FIGS. 27C and 27D show an embolic protection device delivery/recovery catheter with a toggle stop and a distal reduced diameter region with an embolic protection device within the catheter.

DETAILED DESCRIPTION OF THE INVENTION

Inventive aspects of the present disclosure relate to intravascular medical devices having opposite end portions each adapted for insertion within the vasculature of a patient. The opposite end portions each have different operating characteristics such that the medical device is capable of performing different functions depending upon the end of the device that is inserted into the patient. It will be appreciated that the broad aspects of the present invention are applicable to any number of different types of intravascular medical devices. Example devices include guide wires, catheters, implant delivery systems, emboli protection device delivery systems, implant retrieval systems, and emboli protection device retrieval systems.

The components of the catheters of the invention are made from biocompatible materials such as metals or polymeric materials. If necessary, these metals or polymeric materials can be treated to impart biocompatibility by various surface treatments, as known in the art. Suitable materials include stainless steel, titanium and its alloys, cobalt-chromium-nickel-molybdenum-iron alloy (commercially available under the trade designation ELGILOY™), carbon fiber and its composites, and polymers such as liquid crystal polymers, polyetheretherketone (PEEK), polyimide, polyester, high density polyethylene, PEBAX®, various nylons, and the like. A shape memory or superelastic material such as nitinol or shape memory polymer is also suitable. The size, thickness, and composition of materials are selected for their ability to perform as desired as well as their biocompatibility. It is to be understood that these design elements are known to one of skill in the art.

With reference now to the various drawing figures in which identical elements are numbered identically throughout, a description is provided of embodiments that are examples of how inventive aspects in accordance with the principles of the present invention may be practiced. It will be appreciated that the depicted embodiments are merely exemplary, and are not intended to limit the broad scope of the present invention.

I. General Double Ended Device

Figure 1:
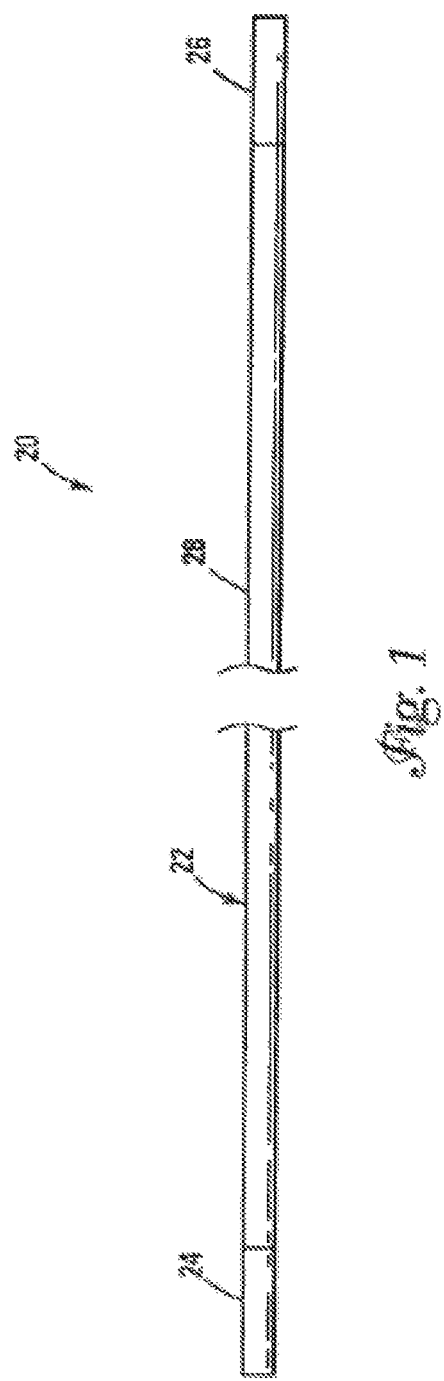
FIG. 1 schematically shows a medical device having features that are examples of inventive aspects in accordance with the principles of the present disclosure.

FIG. 1 illustrates an intravascular medical device 20 having features that are examples of inventive aspects in accordance with the principles of the present disclosure. It will be appreciated that the intravascular medical device 20 can be embodied in a number of different devices such as catheters, guide wires, embolic filter delivery devices, embolic filter retrieval devices, as well as other devices.

Referring to FIG. 1, the medical device 20 includes an elongated body 22 having first and second opposite end portions 24, 26. The elongated body 22 is preferably sufficiently flexible to allow the device to be advanced through a curving vascular pathway without kinking and without puncturing the vessel wall. The first and second end portions 24 and 26 are both capable of leading the elongated member 22 through the vasculature depending upon the direction the elongated member 22 is inserted into the vasculature. The first and second end portions 24 and 26 preferably have different operating characteristics. For example, in one embodiment, the first end portion 24 can be more flexible than the second end portion 26. In other embodiments, the first and second end portions 24 and 26 can have different pre-formed shapes adapted for facilitating advancement of the medical device 20 along different intravascular pathways. In still other embodiments, the first and second end portions 24 and 26 can be adapted for providing different functions. For example, in one embodiment, the first end portion 24 can be adapted for deploying an indwelling medical device such as a stent, graft or embolic protection device, and the second end portion 26 can be adapted for retrieving an indwelling medical device such as a stent, graft or embolic protection device.

The elongated member 22 of the medical device 20 includes a main body 28 that extends between the first and second end portions 24 and 26. The main body 28 can have any number of different types of configurations. For example, the main body 28 can have a solid configuration such as a solid wire configuration, a solid polymeric configuration, or a composite metal and polymeric configuration. In other embodiments, the elongated member 22 can have a tubular configuration defining a single lumen, or can define a plurality of lumens. In one embodiment, the main body 28 includes a metal having "super elastic" properties such as nitinol. The main body 28 can also include materials such as carbon fiber and its composites, liquid crystal polymers, ceramics, and composites in general. The elongated member may be coated with hydrophobic, hydrophilic, or biologically active coatings such as poly vinyl pyrrolidone coatings, ePTFE coatings, or heparin coatings. In one non-limiting embodiment, the elongated member 22 has a length L in the range of 60-300 cm, and an outer diameter D in the range of 0.013" to 0.100" (0.033 to 0.25 cm).

The end portions 24 and 26 of the medical device can have any number of different configurations. For example, end portions 24 and 26 can include a polymeric material, a metal material, a combined polymer and metal material, a shape memory material, or a super elastic material. Further, the end portions 24, 26 can include a solid configuration, or a tubular configuration defining a single lumen or a multi-lumen configuration. Moreover, the end portions 24 and 26 can include constant diameter embodiments, tapered diameter embodiments, solid wall tubular embodiments, perforated wall tubular embodiments, slotted-wall tubular embodiments, coiled embodiments, and any number of other different configurations. The first and second end portions 24 and 26 can be unitary parts of the main body 28, or can be separate pieces or components that are affixed to the main body 28. It will be appreciated that the lengths and diameters of the end portions 24, 26 will vary depending upon their desired operating characteristics. In one embodiment, the end portions 24, 26 function as flexible guide tips having greater flexibility than the main body 28, and different flexibilities from one another.

II. Double Ended Catheter with Rapid Exchange Features

Figure 2:
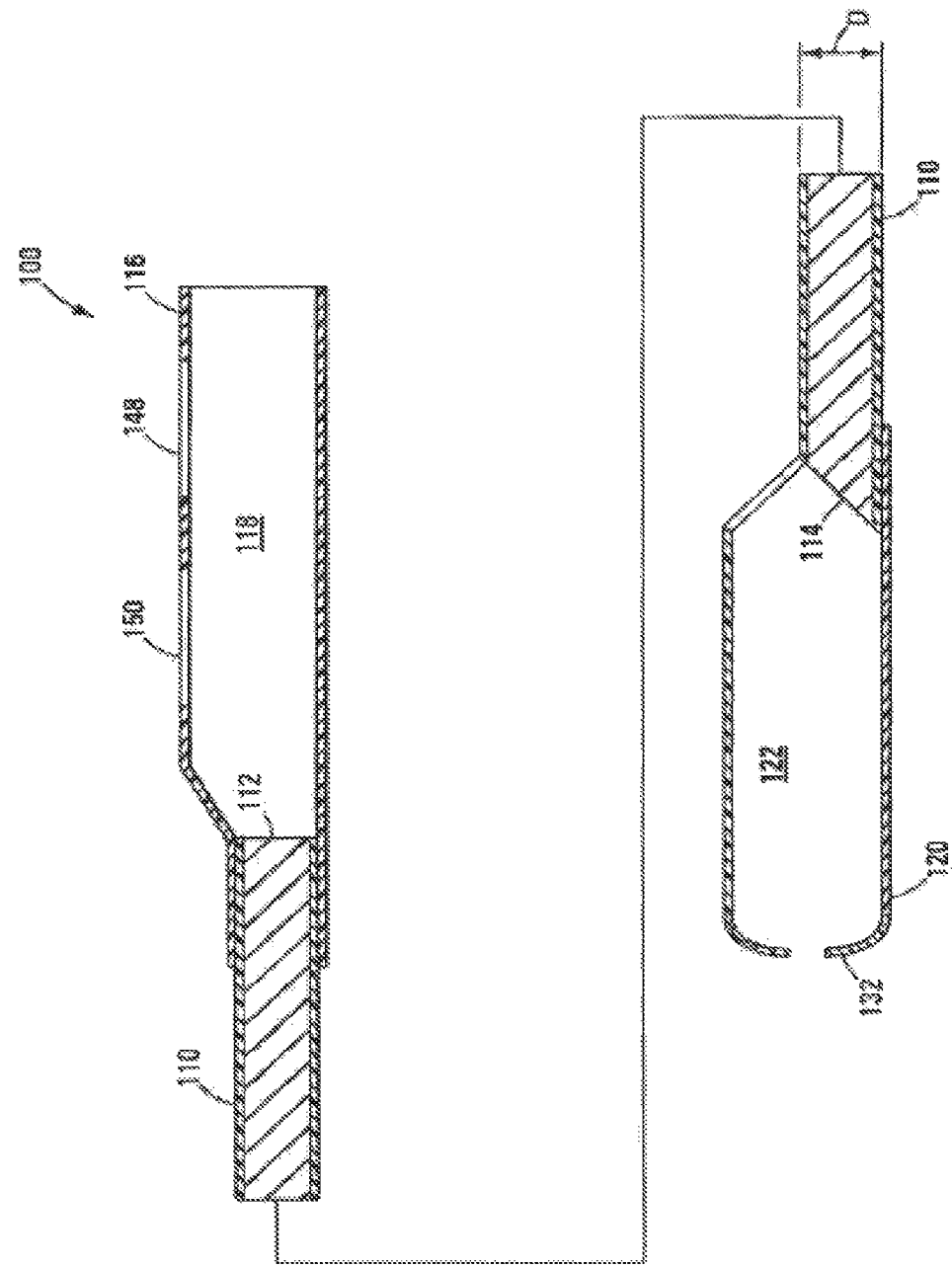
FIG. 2 shows a double-ended catheter having features that are examples of inventive aspects in accordance with the principles of the present disclosure.

FIG. 2 illustrates a catheter 100 having features that are examples of inventive aspects in accordance with the principles of the present disclosure. The catheter 100 includes a central shaft 110 having a first end 112 positioned opposite from a second end 114. A tip in the form of a flexible delivery sheath 116 is positioned at the first end 112. The flexible delivery sheath 116 defines an internal pocket 118 (i.e., a compartment, cavity, enclosure, chamber or receptacle) configured for receiving a preloaded device (e.g., a preloaded embolic protection device such as the filter device 70 shown in FIGS. 3-5). The catheter 100 also includes a flexible retrieval sheath 120 positioned at the second end 114 of the shaft 110. The flexible retrieval sheath 120 defines an internal pocket 122 sized and shaped for receiving a medical device (e.g., an embolic protection device such as the filter device 70 of FIGS. 3-5) for retrieval of the medical device after the device has been used.

The shaft 110 of the catheter 100 is preferably sufficiently flexible and has sufficient column strength to be advanced through the vasculature of a patient. In a preferred embodiment, the shaft 110 includes a solid wire coated with an outer layer of a polymeric material. However, it will be appreciated that in other embodiments, the shaft could include a tubular metal configuration or other configurations. In one non-limiting embodiment adapted for use in coronary applications, the shaft 110 can have a length in the range of 70-170 cm, and more preferably in the range of 100-140 cm. In certain embodiments, the shaft 110 can have an outer diameter D in the range of 0.026"-0.040" (0.066-0.10 cm).

Referring still to FIG. 2, the delivery sheath 116 of the catheter preferably includes a material that is softer and more pliable than the central shaft 110. The flexible design of the delivery sheath 116 facilitates advancing the catheter 100 through tortuous vessels while the more rigid central shaft 110 can provide pushability. In a preferred embodiment, the delivery sheath 116 is formed of a polymer such as LDPE, MDPE, or PEBAX. In one embodiment, the outer diameter of the delivery sheath can be in the range of 0.026-0.040 inches (0.066-0.10 cm), a wall thickness of the delivery sheath can be in the range of 0.001 to 0.005 inches (0.0025 to 0.013 cm), and a length of the delivery sheath can be in the range of 10 to 40 centimeters.

Referring still to FIG. 2, the delivery sheath 116 includes a first sidewall port 148 and a second sidewall port 150. The first and second sidewall ports 148, 150 are spaced apart from one another along the length of the sheath 116. The first sidewall port 148 is located closer to a free end of the sheath 116 than the second sidewall port 150. The ports 148, 150 are preferably skived and dimensioned to allow a distally and inwardly extending wire to extend from the outside of the sheath 116 to the internal pocket 118 at an angle of less than about 10° relative to a longitudinal axis of the catheter 100. Further details regarding the configuration of the flexible sheath can be found in U.S. Patent Application Publication No. 2003/0233117 A1, published Dec. 18, 2003, entitled RAPID EXCHANGE CATHETERS USABLE WITH EMBOLIC PROTECTION DEVICES, the contents of which are hereby incorporated by reference herein.

The recovery sheath 120 of the catheter 100 is preferably made of a compliant material that is more flexible than the shaft 110. Preferably, the sheath 120 has sufficient flexibility to allow the sheath 120 to traverse the tortuous pathways typically encountered within the vasculature of a human. Suitable materials for making the sheath 120 include thermal plastic polymers, polymer blends and thermal set polymers such as silicone, or silicone blends with a low durometer. One such material is a 35/40 D PEBAX blend. Any other appropriate compliant materials may, however, be used. In one embodiment, the outer diameter of the recovery sheath can be in the range of 0.040-0.060 inches (0.10 to 0.15 cm), a wall thickness of the recovery sheath can be in the range of 0.001 to 0.005 inches (0.0025 to 0.013 cm), and a length of the recovery sheath can be in the range of 5 to 30 centimeters.

Referring still to FIG. 2, the recovery sheath has an outermost end that forms a rolled tip 132. The rolled tip 132 is especially designed for crossing a stented or otherwise constricted region of a blood vessel. The rolled tip 132 can also function to capture an implanted device such as an embolic protection device. Further details regarding the recovery sheath 120 can be found in U.S. Patent Application Publication No. 2002/0111649 A1, published Aug. 15, 2002, entitled ROLLED TIP RECOVERY CATHETER, the contents of which are hereby incorporated by reference herein.

In certain embodiments, the sheaths 116, 120 can include one or more bands of radiopaque material, or can be filled with radiopaque material. Examples of radiopaque materials include barium sulfate, bismuth sub carbonate, tungsten powder, and the like. The presence of radiopaque materials facilitates viewing the sheaths under fluoroscopy. The sheaths 116, 120 may be coated with hydrophobic, hydrophilic, or biologically active coatings such as poly vinyl pyrrolidone coatings, ePTFE coatings, or heparin coatings.

Use of the catheter 100 will now be described with respect to a coronary procedure. However, it will be appreciated that the embodiment can also be used for treating other vessels (e.g., carotid, renal, peripheral, and other blood vessels).

In an example of a coronary procedure, a physician first inserts a guidewire (not shown) into the femoral artery of a patient near the groin, and advances the guidewire through the artery, over the aorta and to a coronary ostium 21. Once the guidewire is in place, a guide catheter 11 is passed over the guidewire and advanced until a distal end of the guide catheter 11 is located adjacent the coronary ostium 21. The guidewire (not shown) is then removed. With the guide catheter 11 in place, a coronary guidewire 19 is inserted into the guide catheter and advanced into the coronary artery. See FIG. 3. Next, the proximal end of the coronary guidewire 19 is inserted (i.e. back-loaded) through the distal opening of sheath 116 and then the first sidewall port 148 of the delivery catheter 100.

Figure 3:
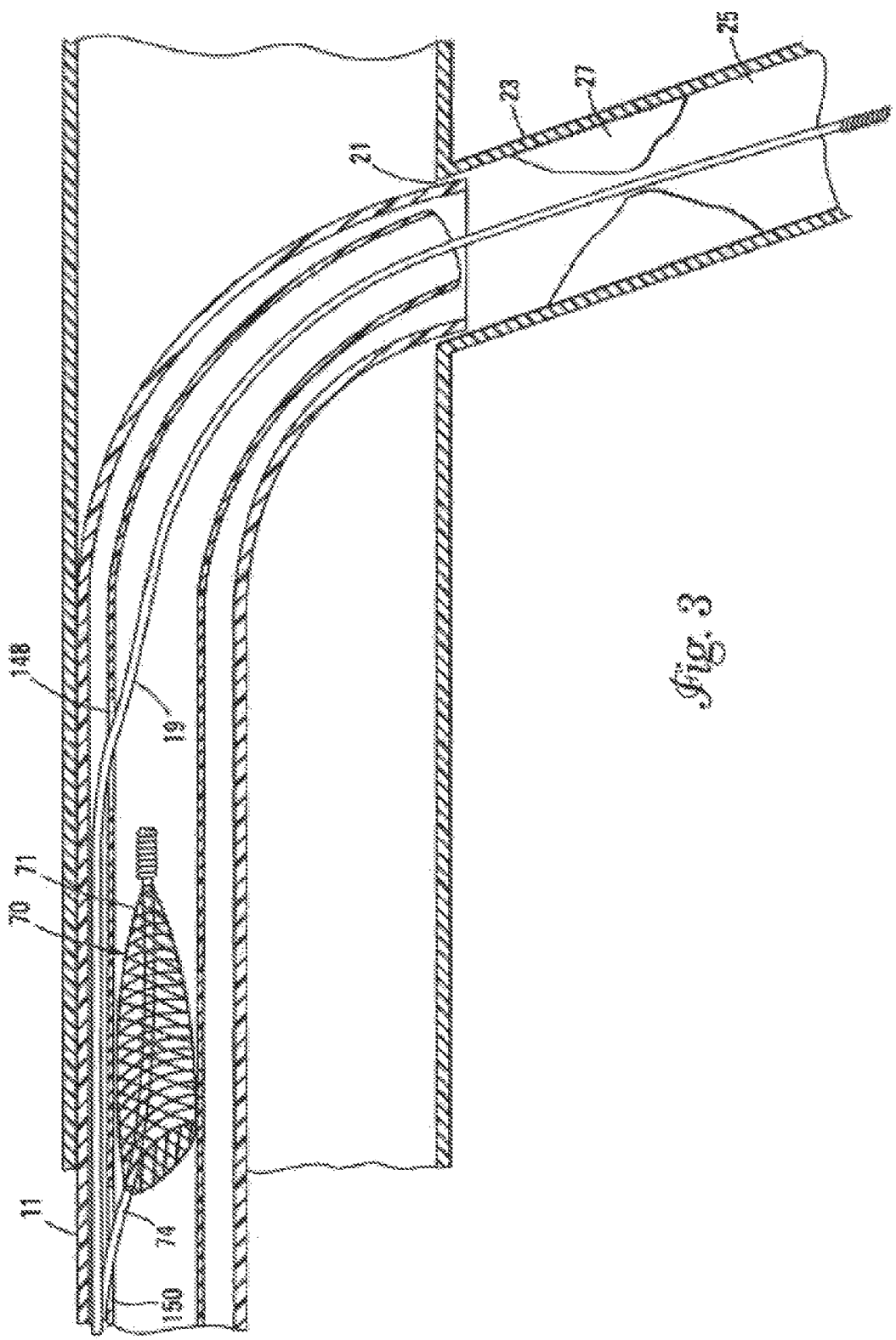
FIG. 3 shows the catheter of FIG. 2 with a delivery end of the catheter containing an emboli protection device, the delivery end is located adjacent to an ostium.

Prior to insertion of the coronary guidewire 19 through the first sidewall port 148, an embolic protection device such as an embolic filter device 70 is preferably pre-loaded within the delivery sheath 116 of the catheter 100. The filter device 70 is preferably a self-expandable filter device such as the filter device disclosed in U.S. Pat. No. 6,325,815, the contents of which are hereby incorporated by reference herein. The filter device 70 includes an expandable filter mesh 71 secured to the distal end of a host wire 74. As shown in FIG. 3, in the pre-loaded configuration, the mesh of the filter device is compressed in a radially reduced profile configuration within the delivery sheath 116, and the host wire 74 extends from the mesh material through the second sidewall port 150 of the delivery sheath 116. The filter device 70 can be viewed as one type of distal emboli protection element. Other distal protection elements which can be included as part of the device are occlusive emboli protection elements, including expandable or inflatable elements for blocking fluid flow through a vessel.

After the guide wire 19 has been back-loaded through the delivery sheath 116, the delivery sheath 116 of the catheter 100 is advanced through the guide catheter 11 along the guidewire 19 until the delivery sheath 116 is advanced to the distal tip the guide catheter 11, as shown in FIG. 3. Preferably, the guidewire 19 is then further advanced within the coronary artery to a point where the distal most tip of the guidewire 19 is located at a target site 25 within a coronary artery 23 (e.g., a site located downstream of a treatment site such as an occlusion 27). The delivery sheath 116 of the catheter 100 can then be tracked along the guide wire 19 to the target site 25 as shown in FIG. 4. In other methods, the guidewire 19 and the catheter 100 can be advanced together across the target site with the guidewire 19 providing stiffening for the catheter 100.

Once the tip of the delivery sheath 116 is located at the target site 25, the guidewire 19 is retracted proximally through the distal sidewall port 148. With the guidewire no longer present within the delivery sheath 116, the filter device 70 can be distally advanced to the tip of the delivery sheath 116 and then from the delivery sheath 116. For example, the embolic filter 70 can be advanced from the sheath 116 by proximally retracting the catheter 100 while the host wire 74 is held in place by the treating physician. By retracting the catheter 100, the sheath 116 retracts relative to the filter device 70 thereby exposing the filter device 70 and allowing the filter device 70 to expand radially so as to provide filtration across the entire cross sectional area of the vessel as shown in FIG. 5.

Once the filter device 70 is in place, the catheter 100 can be retracted from the patient, and an interventional device (e.g., a balloon angioplasty catheter, a stent delivery catheter, an atherectomy device, a thrombectomy device or any other device) can be introduced over the host wire 74 and used to treat the treatment site. As the treatment site is treated, any emboli generated during the treatment process are captured by the filter 70.

After the treatment process has been completed, the interventional device is removed and the catheter 100 is reintroduced over the host wire 74. However, when reintroduced, the catheter 100 is reversed such that the recovery sheath 120 functions as the distal most tip of the catheter 100. Preferably, the host wire 74 is passed through the interior of the recovery sheath 120 as shown in FIG. 6. The catheter 100 is advanced until the rolled end 132 is positioned immediately proximal to the filter device 70. The host wire 74 is then pulled in a proximal direction causing a proximal end of the filter device 70 to contact the rolled tip 132. As the filter device 70 contacts the rolled tip 132, the rolled tip 132 is urged elastically toward an open orientation in which the filter device 70 can be passed into the recovery sheath 120. Once the filter device 70 has been fully drawn into the sheath 120 as shown in FIG. 7, the rolled tip 132 reaches a point where it ceases to be engaged by the filter device 70, and it elastically returns to its undeflected configuration. It will be appreciated that the resilient material forming the sheath 120 prevents the escape of emboli when the filter device 70 is captured. Preferably, at least a portion of the wall of the sheath 120 closely encompasses the periphery of the filter device 70 and assumes the shape of the periphery. As a result, emboli are prevented from passing between the periphery of the filter device 70 and the wall of the sheath 120. Alternatively, the filter device 70 can be partly drawn into the recovery sheath 120 such that only the enlarged proximal opening of the filter is within the sheath.

Once the filter device is positioned within the recovery sheath 120, both the host wire 74 and the catheter 100 can be withdrawn from the patient together as a unit. Thereafter, the procedure is completed by removing the guide catheter 22 from the patient.

III. Over-the-Wire Double Ended Catheter

FIGS. 8 and 9 illustrate an alternative catheter 200 having a similar configuration as the catheter 100 of FIG. 2, except the solid central shaft 110 has been replaced with a double lumen configuration 210 having a first end 212 and a second end 214. The catheter 200 includes a delivery sheath 116 positioned at the first end 212 and a recovery sheath 120 positioned at the second end 114. The double lumen configuration 210 includes a first tube 211 that is coaxial with the delivery sheath 116, and a second tube 213 that is coaxial with the recovery sheath 120. It will be appreciated that the tubes of the double lumen configuration 210 are coupled together and are sufficiently flexible to be able to be passed through a tortuous vascular pathway, and also have sufficient column stiffness to allow the catheter 200 to be pushed through the vasculature. It will be appreciated that the tubes can be manufactured using any number of known techniques. For example, the tubular structures may be extruded or coextruded in the cross sectional shape shown in FIG. 9 or in any number of alternative cross sections, for example those known in the art as double D, smile, or other configurations. Alternatively, the tubular structures can be manufactured from individual tubes of polymer such as polyimide or a super elastic material such as nitinol and held together with adhesives or a thin tube that surrounds both single lumen tubes. It will be appreciated that any number of different types of material can be used to form double lumen configuration 210.

Similar to the previous embodiment, the catheter 200 can be used to both deliver a device such as an embolic protection device, and to retrieve a device such as an embolic protection device. The catheter 200 is used in a manner similar to the catheter 100, except the catheter 200 does not have rapid exchange capabilities. Instead, when the catheter 200 is used with the delivery sheath 116 as the distal end, a guidewire is passed through the entire length of the first tube 211. Similarly, when the retrieval sheath 120 is used as the distal end of the catheter 200, a guidewire or wire such as host wire 74 is passed completely through the second tube 213 of the double lumen configuration 210.

IV. Double Ended Catheter with Combined Rapid Exchange and Over-the-Wire Configuration FIGS. 10 and 11 illustrate another catheter 300 having features that are examples of inventive aspects in accordance with the principles of the present disclosure. Similar to the previous embodiments, the catheter 300 includes a delivery sheath 116 positioned at one end, and a recovery sheath 120 positioned at the opposite end. The delivery sheath 116 and the recovery sheath 120 are interconnected by an elongated central structure 310 that includes a solid shaft 350 coupled to a tubular shaft 352. The solid shaft 350 is connected to the recovery sheath 120, and the tubular shaft 352 is connected to the delivery sheath 116. The elongated central structure is sufficiently flexible to bend through the contours of a tortuous vascular pathway, and also include sufficient column strength to allow the catheter 300 to be pushed through the pathway. The tubular shaft structure 352 has a central lumen in fluid communication with the pocket 118 of the delivery sheath 116.

It will be appreciated that the catheter 300 can be used to deliver devices such as embolic protection devices in much the same way as the previous two embodiments. However, when delivering an embolic protection device using the delivery sheath 116, the delivery sheath 116 as well as the entire tubular shaft 352 would typically be passed over a guidewire. In contrast, when the catheter 300 is used as a retrieval device, the catheter 300 can be used as a rapid exchange catheter in which a guidewire or wire is not passed through the entire catheter, but instead only passes through the distal tip (e.g., the recovery sheath portion 120 of the catheter).

V. Double Ended Catheter with Balloon

FIG. 12 shows another catheter 400 having features that are examples of inventive aspects in accordance with the principles of the present disclosure. The catheter 400 includes a delivery sheath 116 positioned at one end and a recovery sheath 120 positioned at the opposite end. The delivery sheath 116 and the recovery sheath 120 are interconnected by a central elongated member 410. The elongated member 410 includes a solid shaft 411 connected to the recovery sheath 120, and a tubular shaft 413 connected to the delivery sheath 116. The tubular shaft 413 defines a central lumen 415 that extends from a first end 417 of the tubular shaft to the delivery sheath 116. The lumen is preferably sealed so as to not be in fluid communication with the interior of the delivery sheath 116. The delivery sheath 116 includes a guidewire port 148 and a host wire port 150.

Referring still to FIG. 12, a balloon such as an angioplasty balloon or a low pressure occlusion balloon 419 is provided on the tubular shaft 413 adjacent to the delivery sheath 116. The balloon 419 is in fluid communication with the lumen 415 of the tubular shaft 413. The first end 417 of the tubular shaft 413 is sealed by a septum or other seal 421. The septum or seal 421 can include multiple membranes 421a, 421b (see FIG. 12A) bonded together at a perimeter of the membranes. The membrane 421a can have a self-closing slit 425 while membrane 421b can have a central hole that seals against a blunt needle. Either membrane can have a rim 427 that can be sealed to lumen 415 of tubular shaft 413. A syringe with a blunt needle can be used to inject fluid into the lumen through the seal 421 to inflate the balloon 419.

Other techniques can also be used to provide fluid into the lumen. For example, the first end 417 of the tubular shaft 413 can include a side port in fluid communication with a Luer fitting. The Luer fitting provides a connection location for attaching an inflation device. Tuohy Borst fittings can be secured to the tubular shaft at locations distal to and proximal to the side port to provide a seal between the Luer fitting and the catheter body. The Tuohy Borst fittings can also referred to as hemostatic valves.

Figure 13:
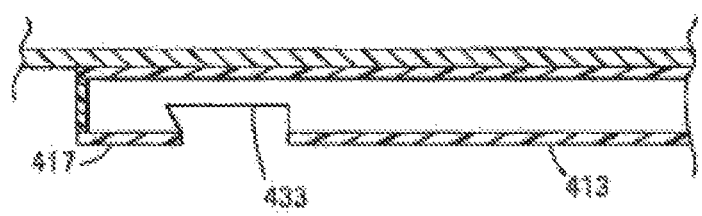
FIGS. 13-15 show a technique for equipping the catheter of FIG. 12 with a Luer fitting for use in inflating and deflating the expandable balloon.
Figure 14:
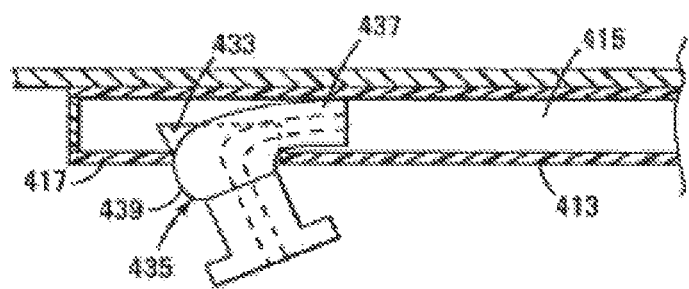
Figure 15:
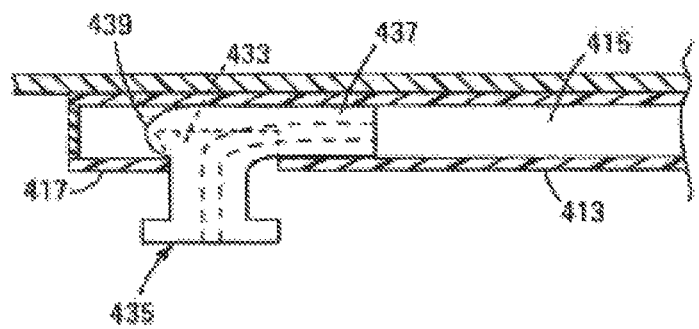

Additionally, a Luer lock fitting can be used to provide fluid to the lumen 415. For example, as shown in FIG. 13, the tubular shaft 413 can include an elongated slot 433 adjacent the first end in which a Luer lock fitting 435 (shown in FIGS. 14 and 15) can be inserted. FIG. 14 shows the Luer lock fitting 435 partially inserted within the slot 433. A stem 437 of the lock fitting 435 fits within the lumen 415. Preferably, the stem 437 snugly fits within the lumen 415 such that friction between the stem 437 and the wall of the tubular shaft 413 function to provide a fluid tight seal about the stem 437. A rounded end 439 of the lock fitting 435 also fits within the slot 433 such that the Luer fitting 435 snaps into a locked or seated position as shown in FIG. 15. The Luer fitting 435 provides an attachment location for attaching a balloon inflation apparatus to the catheter.

It should also be appreciated that the balloon shown in FIG. 12 could alternatively be positioned on the delivery sheath 116 of catheter 400 by those skilled in the art. See, for example, FIG. 12B.

The catheter of FIG. 12B can be used in a manner that helps to prevent distal migration of emboli during embolic filter passage across a treatment site. For example, the catheter can be used as described for catheter 100 in connection with FIGS. 3-7. However, the catheter is preloaded with an actuator style embolic protection device such as that described in U.S. Pat. No. 6,520,978 B1, the contents of which are hereby incorporated by reference herein. Prior to crossing the treatment site, the catheter balloon 419 is inflated to a pressure sufficient to substantially impede blood flow across the treatment site. After balloon inflation, the guidewire 19 is withdrawn and the embolic filter is advanced across the treatment site in a collapsed diameter. Importantly, emboli liberated by the embolic filter during treatment site passage cannot be transported distally because the inflated balloon 419 prevents distal blood flow and distal transport of emboli within the flow stream. After crossing the treatment site, the actuating style filter is actuated to cause it to diametrically enlarge and position the filter across the vessel cross sectional area. At this point, the balloon 419 is deflated and flow is restored, causing emboli liberated during treatment site crossing to be transported to and captured by the filter. The catheter can now be removed and the treatment site treated. Alternatively, the catheter can be advanced and the balloon used to treat a lesion, followed by balloon deflation and capture of released emboli in the filter.

While a balloon has been shown, it will be appreciated that in alternative embodiments, the catheter could include openings for delivering a substance (e.g., a medicine, dye, or other substance) to the vasculature of a patient.

VI. Protective Packaging

Figure 16:
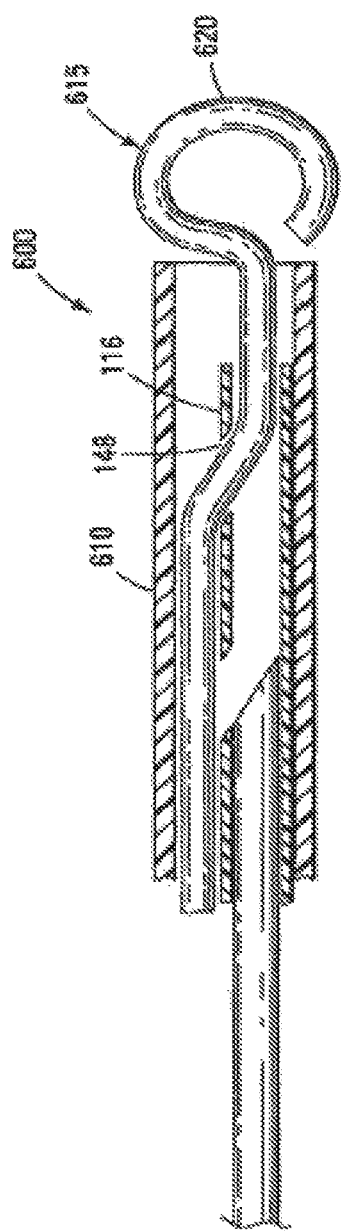
FIGS. 16 and 17 show packaging techniques for protecting the delivery end of the catheter of FIG. 2 during shipping.

FIG. 16 illustrates a system 600 for protecting the delivery sheath 116 during shipping. The system includes an outer protective sheath 610 mounted over the exterior of the delivery sheath 116. A stylette 615 extends into the tip of the delivery sheath 116, through the first sidewall port 148 and along the outer surface of the catheter. The stylette provides rigidity for protecting the delivery sheath 116. A loop 620 is provided for pulling the stylette 615 from the sheath 116.

Figure 17:
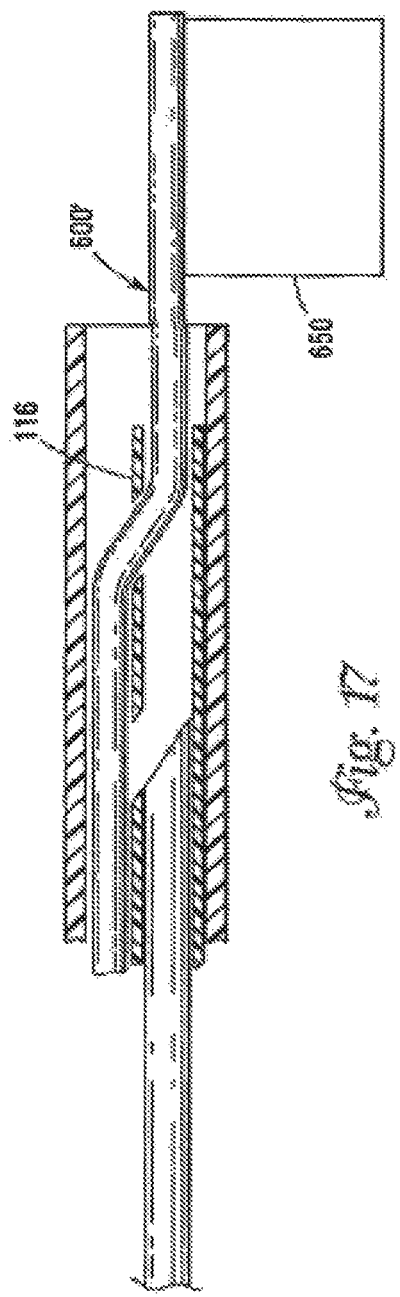

FIG. 17 shows an alternative stylette 600' having a flag 650 as compared to a loop 620. Method of use instructions for the catheter can be printed on the flag 650.

Alternatively the protective packaging can be applied to the recovery sheath 120, or to both the delivery sheath 116 and the recovery sheath 120. It will be further appreciated that it is not necessary to utilize both a stylette and protective sheath; they can be used alone as well as in combination at either or both ends of the catheter.

VII. Double Ended Catheter with Rapid Exchange Features and Variable Diameter

FIG. 18 illustrates a catheter 700 similar to the catheter of FIG. 2. The catheter 700 includes a central shaft 710 having a first end 712 positioned opposite from a second end 714. A tip in the form of a flexible delivery sheath 716 is positioned at the first end 712. The flexible delivery sheath 716 defines an internal pocket 718 (i.e., a compartment, cavity, enclosure, chamber or receptacle) configured for receiving a preloaded device (e.g., a preloaded embolic protection device such as the filter device 770 shown in FIG. 18). The filter device 770 includes an expandable filter mesh 771 secured to the distal end of a host wire 774. The catheter 700 also includes a flexible retrieval sheath 720 positioned at the second end 714 of the shaft 710. The flexible retrieval sheath 720 defines an internal pocket 722 sized and shaped for receiving a medical device (e.g., an embolic protection device such as the filter device 770 of FIG. 18) for retrieval of the medical device after the device has been used.

The delivery sheath 716 includes a first sidewall port 748 and a second sidewall port 750. The first and second sidewall ports 748, 750 are spaced apart from one another along the length of the sheath 716. The first sidewall port 748 is located closer to a free end of the sheath 716 than the second sidewall port 750. The ports 748, 750 are preferably skived and dimensioned to allow a distally and inwardly extending wire to extend from the outside of the sheath 716 to the internal pocket 718 at an angle of less than about 10° relative to a longitudinal axis of the catheter 700.

The catheter 700 includes a lumen portion 740 of a narrower diameter than the internal pocket 718. The diameter of the internal pocket 718 is reduced at constriction 744. Constriction 744 prevents proximal movement of the filter device 770 and creates a preloading stop or "holding zone" location for the filter device 770. This location is distal of the constriction 744 and proximal of the first sidewall port 748 to prevent interaction of the guidewire 719 with the filter 770.

VIII. Guide Wire Loading Assist Device

FIGS. 19 and 19A illustrate a guide wire loading assist device 854. The device 854 has a port 856 that lines up with sidewall port 748 of catheter 700. As shown in FIG. 19, assist device 854 bends catheter 700 to make loading of the guide wire 719 easier. In some embodiments the assist device 854 bends catheter 700 by having a pre-formed shape and stiffness sufficient to overcome the shape and stiffness of catheter 700. Specifically, the device 854 ensures that the guide wire will exit the correct port without interacting with the filter 770.

The device 854 may be loaded prior to packaging or provided as a separate piece within the packaging for the physician to place on the catheter 700 prior to introducing the guide wire 719. A slit 858 that runs from port 856 to the proximal end of the device 854 allows for easy removal of the device once the guide wire is in place. Alternatively, a slit may run from port 856 to distal end of the device 854, or both proximal and distal slits may be provided. In some embodiments, slots are used rather than slits. In another embodiment a pull tab of a size sufficient for a device user to grasp is provided at one or both ends of device 854 for the purpose of facilitating device 854 removal from catheter 700. In some embodiments the device 854 is comprised of a polymer having bright color so as to facilitate rapid identification by the device user. After the device 854 is removed, the catheter reverts to its original conformation.

The device 854 preferably is made of a heat formable material formed with a slight bend. Suitable heat formable materials include polymers such as LDPE, MDPE, and PEBAX. The device 854 can also be injection molded.

Figure 19B:
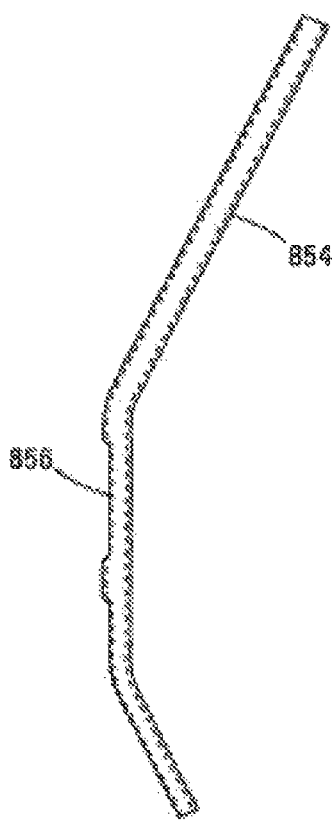
FIGS. 19B and 19C show an alternate embodiment of a guide wire loading assist device.
Figure 19C:
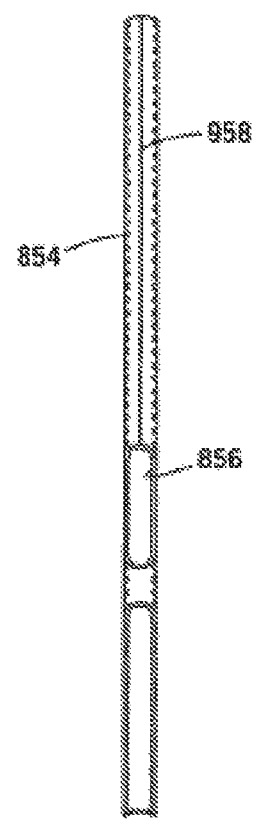

FIGS. 19B and 19C illustrate an alternate embodiment of a guide wire loading assist device 854. The device 854 has a port 856 that lines up with sidewall port 748 of catheter 700. As shown in FIG. 19, assist device 854 bends catheter 700 to make loading of the guide wire 719 easier. In some embodiments the assist device 854 bends catheter 700 by having a preformed shape and stiffness sufficient to overcome the shape and stiffness of catheter 700. Specifically, the device 854 ensures that the guide wire will exit the correct port without interacting with the filter 770.

The device 854 may be loaded prior to packaging or provided as a separate piece within the packaging for the physician to place on the catheter 700 prior to introducing the guide wire 719. A slit 958 runs from port 856 to the distal end of the device 854 and allows for easy removal of the device once the guide wire is in place. A slot runs from a location proximal to port 856 to a proximal end of the device 854. The axis of proximal slotted end of device 854 is oriented approximately 25° away from the axis of the device 854 in the region of port 856. The proximal slotted end of device 854 functions as a pull tab of a size sufficient for a device user to grasp for removal of device 854 from catheter 700. In some embodiments the device 854 is comprised of a polymer having bright color so as to facilitate rapid identification by the device user. After the device 854 is removed, the catheter reverts to its original conformation.

VI. Holding Zone

This invention also provides catheters with a variable inner diameter of the catheter shaft spaced proximally of a guide wire exit port to provide a location or "holding zone" for a distal embolic protection device, such as an embolic filter device. The catheter retains the device in this location during distal advance to the desired intravascular position. In its retained location, the device avoids interference with the guide wire, yet is readily available for deployment when needed.

In one embodiment, the invention provides a catheter for the intravascular deployment of a medical device, the catheter comprising: an elongate tubular body having a proximal portion, a distal portion, a proximal end, a distal end, a lumen extending between the proximal end and the distal end, and a tube wall disposed about the lumen. A first port is disposed in the distal portion of the tubular body and dimensioned to receive a guide wire therethrough, and the first port is formed through the tube wall. The lumen of the tubular body has a first inner diameter at the first port and a second, reduced inner diameter at a point proximal of the first port.

The tip of the catheter may be a generally softer material so as to help prevent damage to a vessel wall as the tip is advanced through the vasculature. Softer materials such as PEBAX®, nylon, rubbers, urethane, silicone, ethylene vinyl acetate, and the like may be attached to the catheter by adhesives, overmolding, heat bonding, solvent bonding, and other techniques known in the art. The tip may have a geometry designed to assist with advancement of the catheter past intraluminal obstructions, such as any of those constructions contained within US 2002/0111649, Rolled Tip Recovery Catheter, the contents of which are hereby incorporated herein in its entirety.

The distal embolic protection device delivery/recovery catheter 1010, 1030, 1050, 1070, shown in the FIGS. 20 to 23 embodiments, has a constriction or narrowing 1012, 1320, 1321, 1322, 1323, 1324, 1325, 1052, 1072 in the inner diameter 1014, 1034, 1054, 1074 of the catheter shaft 1016, 1036, 1056, 1076 proximal of the distal exit port 1018, 1038, 1058, 1078 and proximal of the guide wire exit port 1020, 1040, 1060, 1080, respectively. The catheter 1010, 1030, 1050, 1070 is constructed and designed for use with any suitable guide wire 1100. The constriction or narrowing 1012, 1320, 1321, 1322, 1323, 1324, 1325, 1052, 1072 of the catheter inner diameter 1014, 1034, 1054, 1074, respectively, creates a preloading stop or "holding zone" location for an embolic protection device, such as an embolic filter 1102. This location is distal of the constriction 1012, 1320, 1321, 1322, 1323, 1324, 1325, 1052, 1072 and proximal of the guide wire exit port 1020, 1040, 1060, 1080, respectively, to prevent interaction of the guide wire 1100 with the filter 1102. The guide wire 1100 advances into the distal exit port 1018, 1038, 1058, 1078 and out through the guide wire port 1120, 1040, 1060, 1080, respectively. The catheter 1010, 1030, 1050, 1070 may have the filter 1102 or other device positioned or preloaded for out-of-the-way, non-interfering storage before and during distal advancement of the catheter 1010, 1030, 1050, 1070 over a primary guide wire 1100.

In FIG. 20, the shaft 1016 of the catheter 1010 has an indentation or reduction 1012 of both the inner 1014 and outer diameter 1015 proximal of both the distal exit port 1018 and the guide wire exit port 1020. The proximal side of the indentation 1012 may be a gradual reduction 1017 from the catheter shaft 16 full diameter, while the distal side of the indentation 1012 may be an abrupt or right-angled corner 1019 reduction. The constriction may also be reversed from the FIG. 20 embodiment, with the indentation 1012 distal side having a gradual reduction 1017 from the catheter shaft 1016 full diameter, while the indentation 1012 proximal side has an abrupt or right-angled corner 1019 reduction. Alternatively, both sides of the indentation 1012 may have a gradual or an abrupt reduction from the full diameter, or the constriction 1012 may be formed by any type, shape or method that reduces the diameter of the shaft 1016. The catheter 1010 may be formed with this indentation 1012, for example, by heating and crimping a uniform diameter catheter shaft, for example, with a specially designed tool. Alternatively, a band or wire (not shown) may be slid over the catheter shaft and mechanically deformed by crimping or swaging to effect an indentation, with or without application of heat. This indentation 1012 creates a preloading stop or "holding zone" location for an embolic protection device, such as an embolic filter 1102. The location is distal of the indentation 1012 right-angled corner 1019 and proximal of the guide wire exit port 1020, and is sized and shaped to accommodate any desired embolic protection device, so that the device does not interfere with the guide wire 1100 passing through the guide wire exit port 1020. The cross-sectional area of the indentation 1012 must be large enough to allow free and easy movement of the filter wire 1104, while preventing retraction or passage of the filter 1102 proximal of the indentation 1012. The catheter 1010 can be provided to the physician with the filter 1102 or other device preloaded for out-of-the-way, noninterfering storage during distal advancement of the catheter 1010.

A toroid-shaped insert 1320 constricts or narrows the inner diameter 1034 of the catheter 1030 shaft 1036 proximal of the distal exit port 1038 and proximal of the guide wire exit port 1040 in FIG. 21A. The toroid-shaped insert 1032 may be a thin washer, a short length of tubing, or other alternate structures that allow unencumbered passage of filter wire 1104 yet prevent passage of filter 1102. The walls of the insert 1320 may be curvilinear overall (forming a "donut" shape), may form a right cylinder with an axial cylindrical hole, or any other generally toroidal shape. In some embodiments the outer diameter of the insert 1320 is sized and shaped to fit tightly to the catheter shaft 1036 inner diameter 1034. Alternatively, toroid insert 1320 may be slightly larger in diameter than catheter shaft 1036 inner diameter 1034 and anchored within walls of catheter 1036. The toroid insert 1320 outer diameter may be secured to the inner diameter 1034 by any suitable permanent method, such as a press-fit, heat or re-flow bonding, or adhesive bonding. For example, a toroid insert 1320 can be inserted into catheter shaft 1036 and held at a desired location by mandrels proximal and distal to the insert. The mandrels should be slightly smaller in diameter than catheter inner diameter 1034. The catheter region containing insert 1320 and the mandrels can be inserted into heat shrink tubing and the assembly heated to shrink the heat shrink tubing, melt the catheter 1036 and cause catheter 1036 inside diameter 1034 to conform to the mandrels, thereby immobilizing insert 1320 into the wall of catheter 1036. The cross-sectional area of the opening through the toroid 320 must be large enough to allow free and easy passage of the filter wire 1104, while preventing proximal retraction of the filter 1102 through the toroid 1320. The toroid 1320 forms a constriction or narrowing 1320 of the catheter inner diameter 1034 that creates a preloading stop or "holding zone" location for an embolic protection device, such as an embolic filter 1102. This location is distal of the toroid 1320 and proximal of the guide wire exit port 1040. The filter 1102 or other device can be preloaded for out-of-the-way or non-interfering storage before and during distal advancement of the catheter 1030. In FIG. 21A, a second port 1042 can be used as the exit port for the filter wire 1104. This second port is optionally incorporated into the catheter 1030 and any of the catheter designs disclosed herein can be comprised of this optional second port.

Figure 21K:
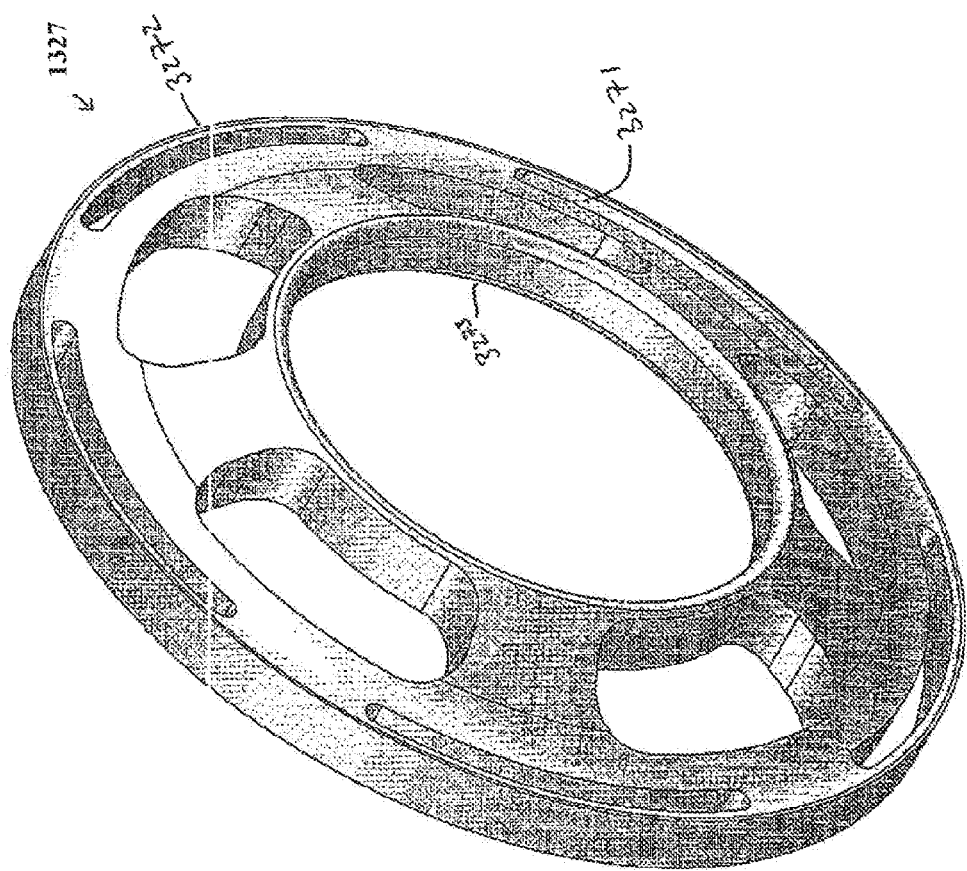
FIG. 21K shows an isometric view of an alternate construction of a toroid insert sized to fit the inner diameter of the catheter shown in FIG. 21A.

FIG. 21K shows a detailed view of a toroidal insert 1327 that constricts or narrows the inner diameter 1034 of the catheter 1030 shaft 1036 proximal of the distal exit port 1038 and proximal of the guide wire exit port 1040. Toroidal insert 1327 may be metal, polymer, ceramic, composite, or any other material that creates a preloading stop or "holding zone" location for an embolic protection device, such as an embolic filter 1102. Toroidal insert 1327 may have coaxial inside 3273 and outside 3274 diameters (shown), non-coaxial inside 3273 and outside 3274 diameters (not shown), and may have irregular inside or outside diameters. Retaining slot 3271 provides an area for polymer to flow into when fusing the insert to the catheter shaft 1036. This flow of polymer into retaining slot 3271 results in an improved bond to the catheter shaft 1036.

Figure 21L:
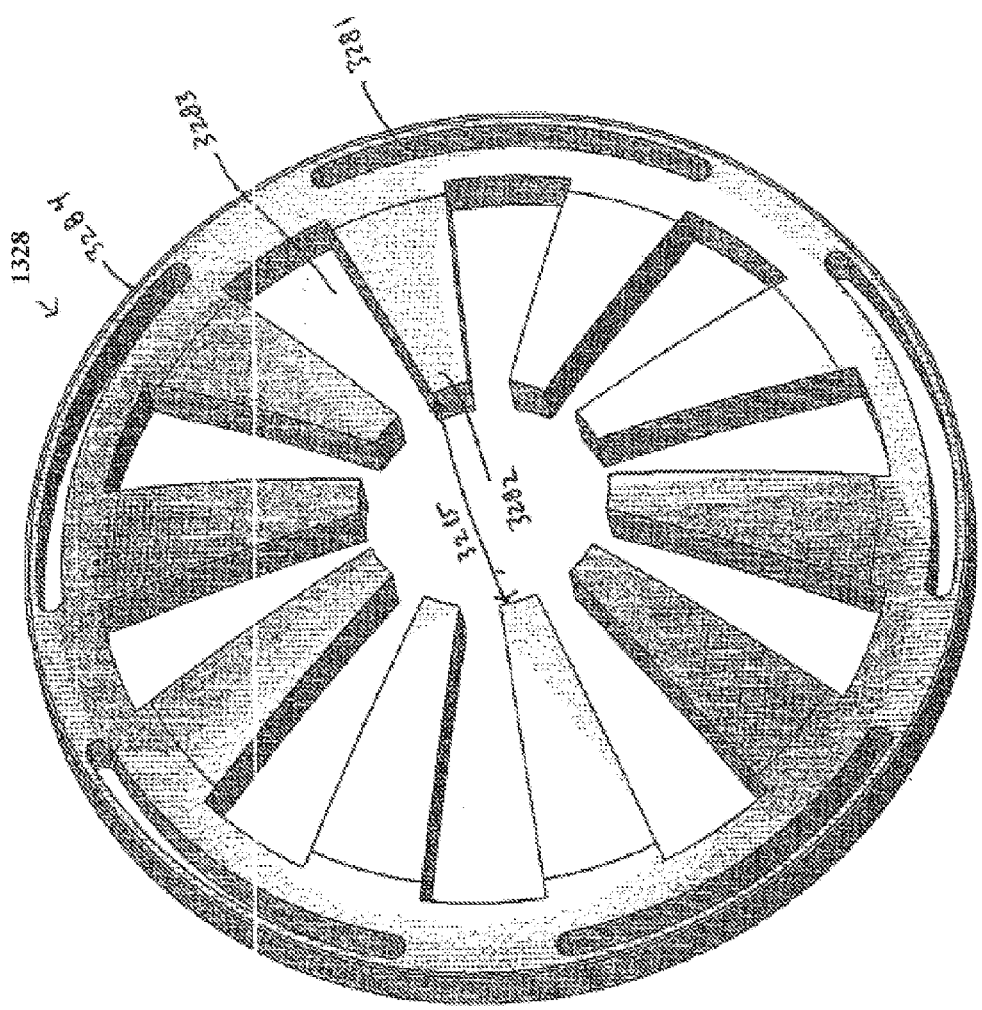
FIG. 21L shows an isometric view of an alternate construction of a toroid insert sized to fit the inner diameter of the catheter shown in FIG. 21A.

FIG. 21L shows a toroidal insert 1328 that constricts or narrows the inner diameter 1034 of the catheter 1030 shaft 1036 proximal of the distal exit port 1038 and proximal of the guide wire exit port 1040. Toroidal insert 1328 may be metal, polymer, ceramic, composite, or any other material that creates a preloading stop or "holding zone" location for an embolic protection device, such as an embolic filter 1102. Toroidal insert 1328 may have coaxial inside 3285 and outside 3284 diameters (shown), non-coaxial inside 3285 and outside 3284 diameters (not shown), and may have irregular inside or outside diameters. Retaining slot 3281 provides an area for polymer to flow into when fusing the insert to the catheter shaft 1036. This flow of polymer into retaining slot 3281 results in an improved bond to the catheter shaft 1036. Toroidal insert 1328 is comprised of fingers 3282 and spaces 3283 which cooperate with filter wire 1104 and filter 1102 to create a preloading stop or "holding zone" location for an embolic protection device, such as an embolic filter 1102, as described below in connection with FIGS. 21D, 21E, and 21M. Toroidal insert 1328 can be made, for example, by laser cutting a tube or a sheet and is comprised of flexible metals such as stainless steel or nitinol, polymers such as polyester, KEVLAR®, or liquid crystal polymers, ceramics, or other materials capable of elastically deforming without significant deformation in this application.

FIG. 21B shows a tubular insert 1321 that constricts or narrows the inner diameter 1034 of the catheter 1030 shaft 1036 proximal of the distal exit port 1038 and proximal of the guide wire exit port 1040. Tubular insert 1321 may be metal, polymer, ceramic, composite, or any other material that creates a preloading stop or "holding zone" location for an embolic protection device, such as an embolic filter 1102. Tubular insert 1321 may have coaxial inside and outside diameters, noncoaxial inside and outside diameters, and may have irregular inside or outside diameters. One example of a preferred tubular insert 1321 with an irregular inside diameter is shown in FIG. 21F. Tubular insert 1321 outer diameter may be secured to the inner diameter 1034 by any suitable permanent method, such as a press-fit, heat or re-flow bonding, adhesive bonding, or other means as are known in the art.

FIG. 21C shows a catheter 1030 similar in many respects to the catheter of FIG. 21B, however the catheter of FIG. 21C is comprised of catheter shaft reinforcement 1041. Catheter shaft reinforcement 1041 can be comprised of braid, coil, strands, slotted tube, or other shapes that are fused or otherwise bonded into catheter shaft 1036 for the purpose of providing bending stiffness and axial stiffness (pushability) to catheter shaft 1036. Catheter shaft reinforcement 1041 can be comprised of metals such as stainless steel or nitinol, polymers such as polyester, KEVLAR®, or liquid crystal polymers, ceramics, or other materials capable of reinforcing catheter shaft 1036.

FIG. 21D shows catheter 1030 with tubular fingered insert 1322. Tubular fingered insert 1322 is anchored to catheter 1036 as described in connection with FIG. 21B. Any of the tubular inserts 1321, 1322 described herein may optionally be provided with holes 1043 to assist with anchoring of insert relative to catheter shaft 1036. Inside diameter of fingered insert 1322 may be as smaller than, equal to, or slightly larger than inside diameter 1034 of catheter 1036.

Figure 21M:
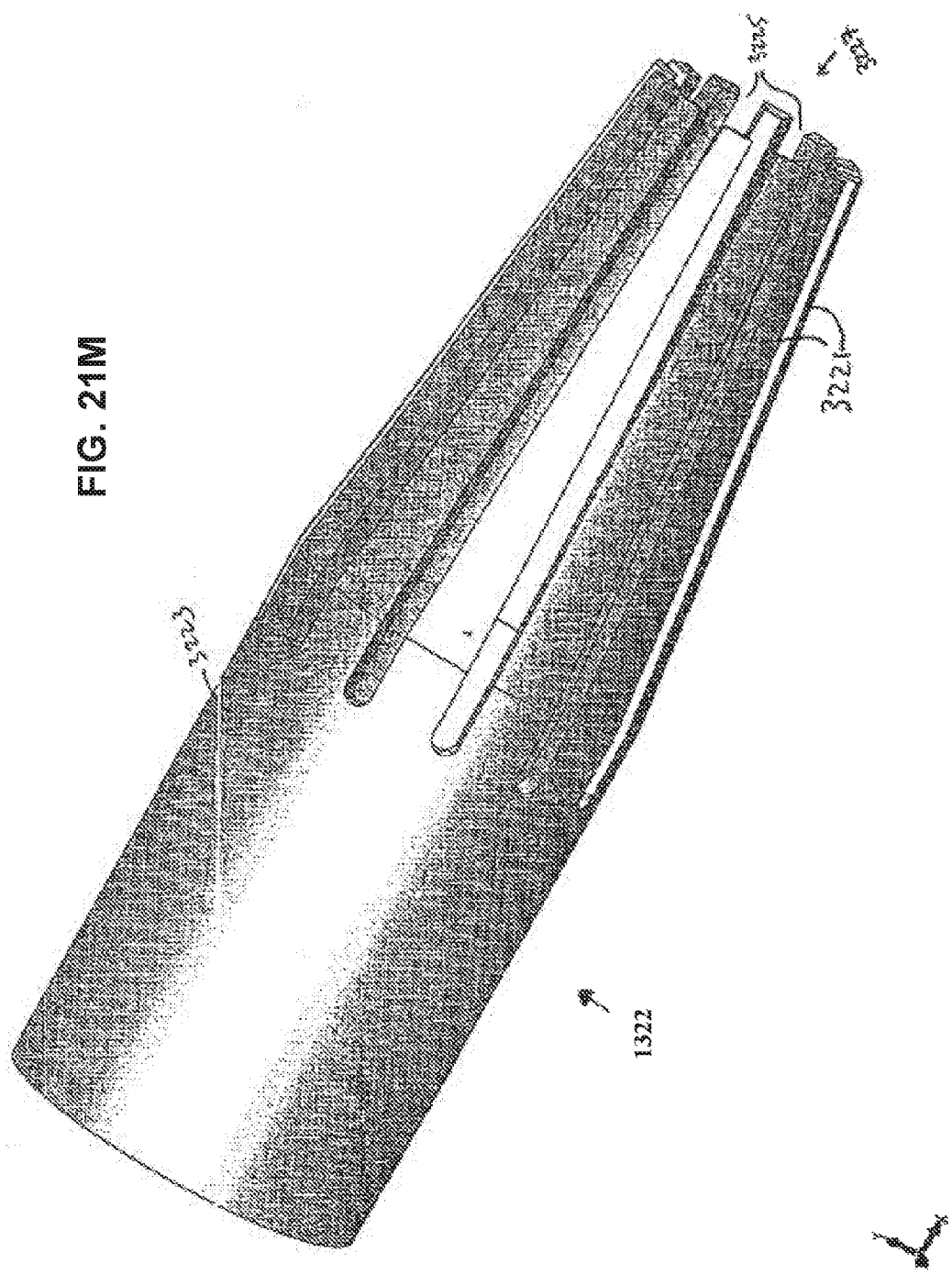
FIG. 21M shows an isometric view of an alternate tubular insert sized to fit the catheter shown in FIG. 21D.

Tubular fingered insert 1322 is shown in greater detail in FIGS. 21E and 21M. Fingered insert 1322 is comprised of at least 2 fingers 3221 attached to a tubular section 3223 and separated by slots 3225. Tubular section 3223 is attached to catheter 1036, fingers 3221 are flexible and can radially flex relative to tubular section 3223. The angle of fingers 3221 relative to the central axis of tubular section 3223 can be varied to suit the particular dimensions of catheter 1036, filter wire 1104, and filter 1102 to effect the needed performance. Fingered insert 1322 can be made, for example, by laser cutting a tube and is comprised of flexible metals such as stainless steel or nitinol, polymers such as polyester, KEVLAR®, or liquid crystal polymers, ceramics, or other materials capable of elastically deforming without significant deformation in this application. Tubular fingered insert 1322 is comprised of end opening 3227 large enough to allow free and easy passage of the filter wire 1104, while preventing proximal retraction of the filter 1102 through the fingered insert 1322. Fingered insert 1322 can be configured to create a preloading stop or "holding zone" location for an embolic protection device, such as an embolic filter 1102.

In use, filter wire 1104 is back loaded through end opening 3227 and filter wire is advanced proximally until filter 1102 contacts fingers 3221. Further proximal advancement of filter 1102 causes fingers 3221 to deflect towards the central axis of catheter 1036 and thereby prevent further proximal advancement of filter 1102. From this position, distal advancement of filter 1102 allows deflection of fingers 3221 to reverse, allowing distal movement of filter 1102 and of filter wire 1104 through end opening 3227.

FIGS. 21G and 21H show catheter 1030 in which the catheter shaft 1036 comprises at least two slots 1324 and at least two strips 1326. Strips 1326 are displaced radially inwardly relative to catheter 1036 axis such that catheter shaft inside diameter 1034 has a constriction 1012 of the inside diameter 1034 proximal of both the distal exit port 1018 and the guide wire exit port 1040. Constriction 1012 may be formed by applying heat to deform strips 1326 or by other means. Constriction 1012 creates a preloading stop or "holding zone" location for an embolic protection device, such as an embolic filter 1102. The location is distal of the constriction 1012 and proximal of the guide wire exit port 1040, and is sized and shaped to accommodate any desired embolic protection device, so that the device does not interfere with the guide wire 1100 passing through the guide wire exit port 1040. The cross-sectional area of the constriction 1012 must be large enough to allow free and easy movement of the filter wire 104, while preventing retraction or passage of the filter 1102 proximal of the constriction 1012. The catheter 1030 can be provided to the physician with the filter 1102 or other device preloaded for out-of-the-way, non-interfering storage during distal advancement of the catheter 1030.

FIGS. 21I and 21J show catheter 1030 in which the catheter shaft 1036 comprises at least two indentations 1325. Indentations 1325 are displaced radially inwardly relative to catheter shaft 1036 axis such that catheter shaft inside diameter 1034 has a constriction 1012 of the inside diameter 1034 proximal of both the distal exit port 38 and the guide wire exit port 1040. Constriction 1012 may be formed by applying heat to deform indentations 1325 or by other means. Constriction 1012 creates a preloading stop or "holding zone" location for an embolic protection device, such as an embolic filter 1102. The location is distal of the constriction 1012 and proximal of the guide wire exit port 1040, and is sized and shaped to accommodate any desired embolic protection device, so that the device does not interfere with the guide wire 1100 passing through the guide wire exit port 1040. The cross-sectional area of the constriction 1012 must be large enough to allow free and easy movement of the filter wire 1104, while preventing retraction or passage of the filter 1102 proximal of the constriction 1012. The catheter 1030 can be provided to the physician with the filter 1102 or other device preloaded for out-of-the-way, non-interfering storage during distal advancement of the catheter 1030.

In FIGS. 22 and 23, a funnel-shaped member 1052, 1072 provides a constriction or narrowing of the inner diameter 1054, 1074 of the shaft 1056, 1076 of the catheter 1050, 1070, respectively. The funnel-shaped member 1052, 1072 is proximal of both the distal exit port 1058, 1078 and the guide wire exit port 1060, 1080, respectively, and may be made of metal, polymer, ceramic, composite, or any other material that creates a preloading stop or "holding zone" location for an embolic protection device, such as an embolic filter 1102. The larger outer diameter of the funnel-shaped member 1052, 1072 is sized and shaped to fit tightly to the catheter shaft 1056, 1076 inner diameter 1054, 1074, respectively. The funnel-shaped member 1052, 1072 outer diameter may be affixed to the inner diameter 1054, 1074, respectively, by any suitable permanent method, such as a press-fit, heat or re-flow bonding, or adhesive bonding. For example, funnel-shaped member 1052, 1072 can be inserted into catheter shaft 1056, 1076 and held at a desired location by mandrels proximal and distal to the member. The mandrels should be slightly smaller in diameter than catheter inner diameter 1054, 1074. The catheter region containing funnel-shaped member 1052, 1072 and the mandrels can be inserted into heat shrink tubing and the assembly heated to shrink the heat shrink tubing, melt the catheter shaft 1056, 1076 and cause catheter shaft 1056, 1076 inside diameter 1054, 1074 to conform to the mandrels, thereby immobilizing funnel-shaped member 1052, 1072 into the wall of catheter shaft 1056, 1076. The inner opening of the member 1052, 1072 may be funnel-shaped corresponding to the exterior shape of the member 1052, 1072. Alternatively, the inner opening may be cylindrical or any other suitable shape. The cross-sectional area of the opening of the funnel-shaped member 1052, 1072 must allow free and easy passage of the filter wire 1104, while preventing proximal retraction of the filter 102 through the member 1052, 1072.

In the FIG. 22 embodiment 1050, the smaller diameter of the funnel-shaped member 1052 faces proximally, and in the FIG. 23 embodiment 1070, the smaller diameter of the funnel-shaped member 1072 faces distally. The funnel-shaped member 1052, 1072 in the catheter inner diameter 1054, 1074, respectively, creates a preloading stop or "holding zone" location for a distal embolic protection device, such as an embolic filter 1102. The filter 1102 or other device can be preloaded to be non-interfering with the guide wire 1100 through the guide wire exit port 1060, 1080.

The embolic protection device delivery/recovery catheter 1090, 1110 shown in the FIGS. 24 and 25 embodiments, has a constriction or narrowing 1092, 1112 in the inner diameter 1094, 1114 of the catheter shaft 1096, 1116 proximal of the distal exit port 1098, 1118 and proximal of the guide wire exit port 1105, 1120, respectively. The axes of the inner diameter 1094, 1114 of the catheter shaft and the inner diameter 1093, 1113 of the proximal portion of the catheter shaft may be substantially coaxial as shown in FIGS. 24 and 25 or may be offset and parallel (not shown). The catheter 1090, 1110 is constructed and designed for use with any suitable guide wire 1100. The constriction or narrowing 1092, 1112 of the catheter inner diameter 1094, 1114, respectively, creates a preloading stop or "holding zone" location for a distal embolic protection device, such as an embolic filter 1102. This location is distal of the constriction 1092, 1112 and proximal of the guide wire exit port 1105, 1120, respectively, to prevent interaction of the guide wire 1100 with the filter 1102. The guide wire 1100 advances into the distal exit port 1098, 1118 and out through the guide wire port 1105, 1120, respectively. The catheter 1090, 1110 may have the filter 1102 or other device positioned or preloaded for out-of-the-way, non-interfering storage before and during distal advancement of the catheter 1090, 1110 over a primary guide wire 1100.

The catheter of FIGS. 24 and 25 has the advantage of providing transverse support to filter wire 1104. It is advantageous to taper the diameter of filter wire 1104 such that the diameter of the filter wire 1104 near the filter 1102 is reduced compared to the diameter of the filter wire 5-20 cm proximal to the filter 1102. Filter wires so tapered can buckle when they are used to distally advance a filter out of a catheter such catheter 1090, 1110 respectively. By reducing the inner diameter 1093, 1113 of the proximal portion of the catheter shaft 1096, 1116 respectively, lateral support is provided to a tapered filter wire 1104 during distal advancement of filter 1102 from the catheter. Said lateral support can help prevent filter wire 1104 buckling.

In FIGS. 24 and 25, the shaft 1096, 1116 of the catheter 1090, 1110 has an indentation or reduction 1092, 1112 of both the inner 1094, 1114 and outer diameter 1095, 1115 proximal of both the distal exit port 1098, 1118 and the guide wire exit port 1105, 1120. In FIG. 24, the proximal side of the indentation 1092 is an abrupt or right-angled corner 1097 reduction from the catheter shaft 1096 full diameter, and the distal side of the indentation 1092 is an abrupt or right-angled corner 1099 reduction. The inner diameter 1093 of the proximal portion of the shaft 1096 is less than the inner diameter 1094 of the distal portion of the shaft. In FIG. 25, the reduction 1112 is a gradual reduction from the catheter shaft 1116's largest inner diameter 1114. The inner diameter 1113 of the proximal portion of the shaft 1116 is less than the inner diameter 1114 of the distal portion of the shaft.

The reduction or indentation 1092, 1112 creates a preloading stop or "holding zone" location for a distal embolic protection device, such as an embolic filter 1102. The location is distal of the reduction 1092, 1112 and proximal of the guide wire exit port 1105, 1120, and is sized and shaped to accommodate any desired distal embolic protection device or other device, so that the device does not interfere with the guide wire 1100 passing through the guide wire exit port 1105, 1120. The cross-sectional area of the indentation 1092, 1112 at its narrowest point must be large enough to allow free and easy movement of the filter wire 1104, while preventing retraction or passage of the filter 1102 proximal of the indentation 1092, 1112. The catheter 1090, 1110 can be provided to the physician with the filter 1102 or other device preloaded for out-of-the-way, non-interfering storage during distal advancement of the catheter 1090, 1110.

The embolic protection device delivery/recovery catheter 1130 shown in FIGS. 26A and 26B has a constriction or narrowing 1132 in the inner diameter 1094 of the catheter shaft 1096 proximal of the distal exit port 1098 and proximal of the guide wire exit port 1105. The axes of the inner diameter 1094 of the catheter shaft and the inner diameter 1093 of the proximal portion of the catheter shaft are offset and substantially parallel. The catheter 1130 is constructed and designed for use with any suitable guide wire 1100. The constriction or narrowing 1132 of the catheter inner diameter 1094 creates a preloading stop or "holding zone" location for a distal embolic protection device, such as an embolic filter 1102. This location is distal of the constriction 1132 and proximal of the guide wire exit port 1105 to prevent interaction of the guide wire 1100 with the filter 1102. The guide wire 1100 advances into the distal exit port 1098 and out through the guide wire port 1105. The catheter 1130 may have the filter 1102 or other device positioned or preloaded for out-of-the way, non-interfering storage before and during distal advancement of the catheter 1130 over a primary guide wire 1100.

Additionally, the embolic protection device delivery/recovery catheter 1130 shown in FIGS. 26A and 26B, has a stiffening member 1134 embedded in wall of catheter 1096. Stiffening member 1134 may comprise metal, polymer, ceramic, composite, or any other material that imparts bending stiffness and columnar stiffness to proximal portion of catheter shaft 1096 for the purpose of improved catheter pushability and trackability through the vasculature of a patient. By way of example, catheter shaft 1096 may be comprised of a two lumen extrusion as shown in FIG. 26B with stiffening member 1134 within one of the lumens. Distal portion 1136 of catheter 1096 may be a single lumen tube attached to two lumen tube of catheter 1096 by heat fusing by means of mandrels and heat shrink tubing in a manner similar to that described above in connection with FIG. 21A using methods well known to those of skill in the art.

The embolic protection device delivery/recovery catheter 1150 shown in FIGS. 26C and 26D has a constriction or narrowing 1152 in the inner diameter 1094 of the catheter shaft 1096 proximal of the distal exit port 1098 and proximal of the guide wire exit port 1105. The axes of the inner diameter 1094 of the catheter shaft and the inner diameter 1093 of the proximal portion of the catheter shaft are offset and substantially parallel. The catheter 1150 is constructed and designed for use with any suitable guide wire 1100. The constriction or narrowing 1152 of the catheter inner diameter 1094 creates a preloading stop or "holding zone" location for a distal embolic protection device, such as an embolic filter 1102. This location is distal of the constriction 1152 and proximal of the guide wire exit port 1105 to prevent interaction of the guide wire 1100 with the filter 1102. The guide wire 1100 advances into the distal exit port 1098 and out through the guide wire port 1105. The catheter 1150 may have the filter 1102 or other device positioned or preloaded for out-of-the way, non-interfering storage before and during distal advancement of the catheter 1150 over a primary guide wire 1100.

The catheter of FIGS. 26A to 26D has the advantage of providing transverse support to filter wire 1104. It is advantageous to taper the diameter of filter wire 1104 such that the diameter of the filter wire 1104 near the filter 1102 is reduced compared to the diameter of the filter wire 5-20 cm proximal to the filter 1102. Filter wires so tapered can buckle when they are used to distally advance a filter out of a catheter such catheter 1130, 1150 respectively. By reducing the inner diameter 1093 of the proximal portion of the catheter shaft 1096, lateral support is provided to a tapered filter wire 1104 during distal advancement of filter 1102 from the catheter. Said lateral support can help prevent filter wire 1104 buckling.

Additionally, the embolic protection device delivery/recovery catheter 1150 shown in FIGS. 26C and 26D, has a stiffening member 1154 embedded in wall of 1010 catheter 1096. Stiffening member 1134 may comprise metal, polymer, ceramic, composite, or any other material that imparts bending stiffness and columnar stiffness to proximal portion of catheter shaft 1096 for the purpose of improving catheter pushability and trackability through the vasculature of a patient. By way of example, catheter shaft 1096 may be comprised of a heat shrink tubing as shown in FIG. 26D with stiffening member 1134 and catheter shaft within the lumen of the heat shrink tubing 1156 and held in close apposition thereby.

The embolic protection device delivery/recovery catheter 1170 shown in FIGS. 27A to 27D has a constriction or narrowing effected by toggle 1172 in the inner diameter 1094 of the catheter shaft 1096 proximal of the distal exit port (not shown) and proximal of the guide wire exit port (not shown). The axes of the inner diameter 1094 of the catheter shaft and the effective inner diameter 1093 of the proximal portion of the catheter shaft are offset and substantially parallel. The catheter 1170 is constructed and designed for use with any suitable guide wire 1100. The constriction or narrowing effected by toggle 1172 creates a pre loading stop or "holding zone" location for a distal embolic protection device, such as an embolic filter 1102. This location is distal of the constriction effected by toggle 1172 and proximal of the guide wire exit port to prevent interaction of the guide wire 1100 with the filter 1102. The guide wire 1100 advances into the distal exit port and out through the guide wire port. The catheter 1170 may have the filter 1102 or other device positioned or preloaded for out-of-the-way, non-interfering storage before and during distal advancement of the catheter 1170 over a primary guide wire 1100.

Additionally, the embolic protection device delivery/recovery catheter 1170 shown in FIGS. 27A to 27D has a distal diameter reduced portion 1182 of catheter 1096. Diameter reduced portion 1182 of catheter 1096 may be formed by necking, swaging, or other means as are known in the art. Diameter reduced portion 1182 of catheter 1096 advantageously provides a reduced lesion crossing profile to catheter 1096. Any of the catheters described herein may be comprised of diameter reduced portion 1182.

Toggle 1172 and toggle pivot 1174 may comprise metal, polymer, ceramic, composite, or any other material that has enough strength to prevent passage of filter proximally past toggle 1172. Toggle pivot is embedded in catheter 1096 within pocket 1176. Pocket 1176 allows toggle to move relatively freely about toggle pin 1174. Catheter 1096 may be reinforced (not shown), for example with metals, in the vicinity of toggle pin to prevent toggle pin 1174 from tearing out of catheter 1096 during use.

Toggle 1172 effects a constriction or narrowing and thereby creates a preloading stop or "holding zone" location for a distal embolic protection device, such as an embolic filter 1102 as follows. Filter wire is back loaded into distal exit port (not shown) and past toggle 1172 as shown in FIG. 27C. As filter wire 1104 traverses toggle 1172 toggle will pivot, allowing filter wire 1104 to pass through effective inner diameter 1093. Further proximal advancement of filter wire 1104 will cause enlarged proximal end of filter 1106 to contact distal face 1178 of toggle, and still further proximal advancement of filter wire 1104 will cause causing toggle 1172 to pivot about toggle pin 1174 and decrease effective inner diameter 1093 by moving proximal toggle arm 1177 towards the opposing wall 1175 of catheter 1096. Proximal advancement of filter wire 1104 will cease when enlarged proximal end of filter 1106 contacts proximal toggle arm 1177.

The following general details of the construction and operation of the inventive catheter apply to all embodiments, with specific details for individual embodiments as noted. Preferably, the catheter of this invention has a guide wire exit port located from 5 to 30 cm from the catheter distal tip. Proximal of the guide wire exit port is a constriction that creates a reduction of the size of the inner diameter of the catheter shaft. The distance between the guide wire exit port and the constriction can be made to accommodate the size and shape of the specific distal embolic protection device or other device to be retained.

The catheter inner diameter can be reduced or necked down by any suitable configuration of the overall cross-sectional area that will permit unimpeded passage for a distal embolic protection device wire, while preventing retraction of the device proximal of the constriction. The constriction or diameter reduction can be abrupt, gradual or tapered, or any combination or multiple series of abrupt or gradual tapers or reductions. Additional non-limiting examples of the desired constriction include indentations or dimples within the catheter wall, an intraluminal net or meshwork, or use of a pin transverse to the catheter axis. Additional guide wire exit port(s) may be located proximal of this constriction or diameter reduction.

An exemplar use of the catheters described herein is as follows. A guide catheter is introduced from the groin of the patient, through the femoral artery, and to the ostium of a coronary vessel as previously described and as is well known in the art. A coronary guidewire is threaded through the guidewire and into a coronary vessel to a region of interest. An embolic protection device filter wire 1104 is back loaded into the distal exit port of an inventive catheter, through the constriction or narrowing, and proximally through the inventive catheter. The filter wire is advanced proximally until the filter 1102 is positioned or pre-loaded within the catheter and abuts the distal portion of the constriction or narrowing in a preloaded, out-of-the-way, non-interfering storage position. The coronary guidewire is next back loaded into the distal exit port of an inventive catheter and out of the catheter through the guide wire port located distal to the constriction or narrowing. Next the inventive catheter is advanced distally along the guidewire to a region of interest. The guidewire is withdrawn from the patient and catheter is withdrawn proximally relative to the embolic filter 1102, whereby the filter deploys or is deployed and the inventive catheter is withdrawn from the patient.

To recover the embolic device the proximal end of the filter wire 1104 is back loaded into the distal exit port of an inventive catheter and the catheter advanced distally to the immediate proximity of the filter. The filter is then drawn into the inventive catheter and the inventive catheter removed from the patient.

The catheter of this invention provides many advantages for the physician and the patient. The catheter inner diameter constriction provides a location to preload an embolic protection device and allows the physician to use a guide wire of choice to position the catheter intravascularly. Typical over-the-wire or rapid-exchange catheter designs may allow a physician to use a favored guide wire for catheter positioning, but do not provide a preloaded device in a non-interfering position, as does the present catheter. The catheter may be constructed to accept any type, shape or size of embolic protection device or other device. The physician may obtain the catheter with a pre-loaded device of choice. The use of the catheter with a preloaded device reduces the distance the catheter must travel, in comparison to a conventional delivery/recovery catheter, thus reducing intravascular manipulation by reducing the number of catheter exchanges, lessening trauma to the patient, and the length of time for the procedure. The catheter with a preloaded device allows correct positioning of the embolic device every time, while preventing interaction of the guide wire with the device. The present catheter improves overall ease of use both in construction of the catheter, in positioning the catheter within the patient, and in deploying the embolic protection device.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

The invention claimed is:

1. A catheter for the intravascular deployment of a medical device, the catheter comprising:
   an elongate tubular body having a proximal portion, a distal portion, a proximal end, and a distal end, wherein the elongate tubular body defines a lumen extending between the proximal end and the distal end;
   wherein the distal portion of the elongate tubular body defines a first port formed through a tube wall of the elongate tubular body into the lumen at the distal portion, wherein the first port is disposed proximal to the distal end of the elongate tubular body, wherein the first port is dimensioned to receive a guide wire therethrough, and wherein the lumen defines a first inner diameter at the first port and a second inner diameter less than the first inner diameter at a position proximal to the first port; and
   wherein the distal portion comprises a transition point proximal to the first port at which the diameter of the lumen transitions from the first inner diameter to the second inner diameter.

2. The catheter of claim 1, wherein the tube wall of the elongate tubular body has a substantially uniform wall thickness.

3. The catheter of claim 1, wherein a toroid-shaped insert is disposed in the lumen of the elongate tubular body perpendicular to a longitudinal axis of the lumen at the transition point to reduce the lumen from the first inner diameter to the second inner diameter.

4. The catheter of claim 3, wherein the toroid-shaped insert is a washer.

5. The catheter of claim 1, wherein a funnel-shaped insert is disposed in the lumen of the elongate tubular body along a longitudinal axis of the lumen at the transition point to reduce the lumen from the first inner diameter to the second inner diameter.

6. The catheter of claim 5, wherein the funnel-shaped insert has a larger opening directed towards the distal end of the elongate tubular body.

7. The catheter of claim 1, wherein the lumen of the elongate tubular body has the second inner diameter extending over a substantial portion of the elongate tubular body along a longitudinal axis of the lumen.

8. The catheter of claim 1, wherein the elongate tubular body comprises an abrupt reduction in inner diameter at the transition point from the first inner diameter to the second inner diameter.

9. The catheter of claim 1, wherein the elongate tubular body comprises a gradual reduction in inner diameter at the transition point from the first inner diameter to the second inner diameter.

10. The catheter of claim 1, wherein the elongate tubular body defines a second port formed through the tube wall of the elongate tubular body into the lumen at the distal portion of the elongate tubular body and proximal to the transition point, wherein the second port is configured to receive a host wire for the medical device.

11. The catheter of claim 10, wherein the second port is disposed from 5 to 20 centimeters proximal of the first port.

12. The catheter of claim 1, wherein the first port is disposed from 5 to 30 centimeters from the distal end of the elongate tubular body.

13. The catheter of claim 1, wherein the first port has a maximum dimension of less than 0.040 inch.

14. The catheter of claim 1, wherein the first port has a maximum dimension of less than 0.020 inch.

15. The catheter of claim 1, wherein the catheter has an outer diameter of less than 0.040 inch.

16. An assembly comprising:
    the catheter of claim 1; and
    a host wire comprising an embolic protection device at one end, wherein the embolic protection device is disposed within the lumen of the elongate tubular body distal to the transition point and proximal to the first port;
    wherein the transition point and the embolic protection device are sized to prevent the embolic protection device from moving proximally across the transition point.

17. The assembly of claim 16, wherein the elongate tubular body defines a second port formed through the tube wall of the elongate tubular body into the lumen at the distal portion of the elongate tubular body and proximal to the transition point, wherein the host wire extends through the second port.

18. The assembly of claim 16, wherein the distal portion of elongate tubular body comprises a delivery sheath configured to deliver the embolic protection device through the distal end of the elongate tubular body, and wherein the proximal portion of the elongate tubular body comprises a retrieval sheath configured to receive the embolic protection device through the proximal end after being delivered through the distal end.

19. The assembly of claim 18, wherein the proximal portion of the elongate tubular body defines a third port formed through the tube wall of the elongate tubular body into the lumen, wherein the third port is configured to receive the host wire during the retrieval of the embolic protection device through the proximal end.

20. The catheter of claim 1, wherein the distal portion of elongate tubular body comprises a delivery sheath configured to deliver an embolic protection device through the distal end of the elongate tubular body, and wherein the proximal portion of the elongate tubular body comprises a retrieval sheath configured to receive the embolic protection device through the proximal end after being delivered through the distal end.

\* \* \* \* \*